(12) United States Patent
Chen et al.

(10) Patent No.: US 8,618,360 B2
(45) Date of Patent: Dec. 31, 2013

(54) RICE TRANSGENIC EVENT 17314 AND METHODS OF USE THEREOF

(75) Inventors: Yun-Chia Sophia Chen, Milpitas, CA (US); Can Duong, St. Louis, MO (US); Sio-Wai Hoi, St. Louis, MO (US); Christopher S. Hubmeier, Ballwin, MO (US); Youlin Qi, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 101 days.

(21) Appl. No.: 13/146,634

(22) PCT Filed: Mar. 29, 2010

(86) PCT No.: PCT/US2010/029092
§ 371 (c)(1),
(2), (4) Date: Nov. 30, 2011

(87) PCT Pub. No.: WO2010/117735
PCT Pub. Date: Oct. 14, 2010

(65) Prior Publication Data
US 2012/0066791 A1 Mar. 15, 2012

Related U.S. Application Data

(60) Provisional application No. 61/164,895, filed on Mar. 30, 2009.

(51) Int. Cl.
*C12N 15/82* (2006.01)
*C07H 21/02* (2006.01)
*C12Q 1/68* (2006.01)
*A01H 5/00* (2006.01)
*A01H 1/00* (2006.01)

(52) U.S. Cl.
USPC ........ 800/300; 536/24.3; 435/6.1; 800/320.2; 800/295; 800/266

(58) Field of Classification Search
USPC ........................................... 800/300
See application file for complete search history.

(56) References Cited

U.S. PATENT DOCUMENTS

| | | | |
|---|---|---|---|
| 7,250,556 B2 | 7/2007 | Wessler et al. | |
| 7,563,945 B2 | 7/2009 | Conner et al. | |
| 7,575,917 B2 | 8/2009 | Gilbertson et al. | |
| 7,855,323 B2 | 12/2010 | Huang et al. | |
| 7,868,149 B2 | 1/2011 | Boukharov et al. | |
| 7,960,610 B2 | 6/2011 | Armstrong et al. | |
| 2004/0214783 A1* | 10/2004 | Terman ........................ | 514/33 |
| 2006/0150268 A1 | 7/2006 | Martin et al. | |
| 2007/0039076 A1* | 2/2007 | Boukharov et al. ........ | 800/320.2 |
| 2008/0227639 A1 | 9/2008 | Wu et al. | |

FOREIGN PATENT DOCUMENTS

| | | |
|---|---|---|
| CN | 101302520 A | 11/2008 |
| EP | 1572901 B1 | 9/2012 |

OTHER PUBLICATIONS

Hohe et al, A tool for understanding homologous recombination in plants, Plant Cell Rep. (2003) 21:1135-1142.*
Matsumoto et al, *Oryza glaberrima* DNA, GenBank Accession No. FT824634, Direct Submission, Submitted Jul. 28, 2010.*
GenBank Accession No. BX957292.1, dated Jan. 15, 2009.
GenBank Accession No. XM002180906.1, dated Jan. 21, 2009.
Genbank Direct Submission BU722017.1 titled "SJM2CEGO6 SKM *Schistosoma japonicum* cDNA similar to dbjBAB26956.1 (AK010461) putative [*Mus musculus*], mRNA sequence" (Oct. 23, 2003) [retrieved from the internet Nov. 4, 2011]; <http://www.ncbi.nlm.nih.gov/nucest/28329364>); p. 1, polynucleotide sequence.
Genbank: CR380953.1. *Candida glabrata* strain CB138 chromosome G complete sequence. 2008 [retrieved from the Internet Nov. 4, 2011: http://www.ncbi.nlm.nih.gov/nuccore/49525678>].
GenBank: AL731758.4. *Oryza sativa* chromosome 12, BAC OSJNBa0029K06 of library OSJNBa from chromosome 12 of cultivar Nipponbare of ssp. Japonica of *Pryza sativa* (rice), complete sequence (Jan. 19, 2004) [retrieved from the internet Nov. 4, 2011]. New England BioLabs Inc. 1998/99 Catalog, (NEB Catalog) , pp. 121 and 284, undated.
Final Office Action regarding U.S. Appl. No. 11/801,114, dated Aug. 26, 2009.

* cited by examiner

*Primary Examiner* — David H Kruse
*Assistant Examiner* — Mykola Kovalenko
(74) *Attorney, Agent, or Firm* — Dentons US LLP; Pamela Sisson

(57) ABSTRACT

The present invention provides a transgenic rice event 17314 and plants, plant cells, seeds, plant parts, and commodity products derived from event 17314. The present invention also provides polynucleotides specific for event 17314 and plants, plant cells, seeds, plant parts, and commodity products comprising polynucleotides specific for event 17314. The invention also provides methods related to event 17314.

39 Claims, 1 Drawing Sheet

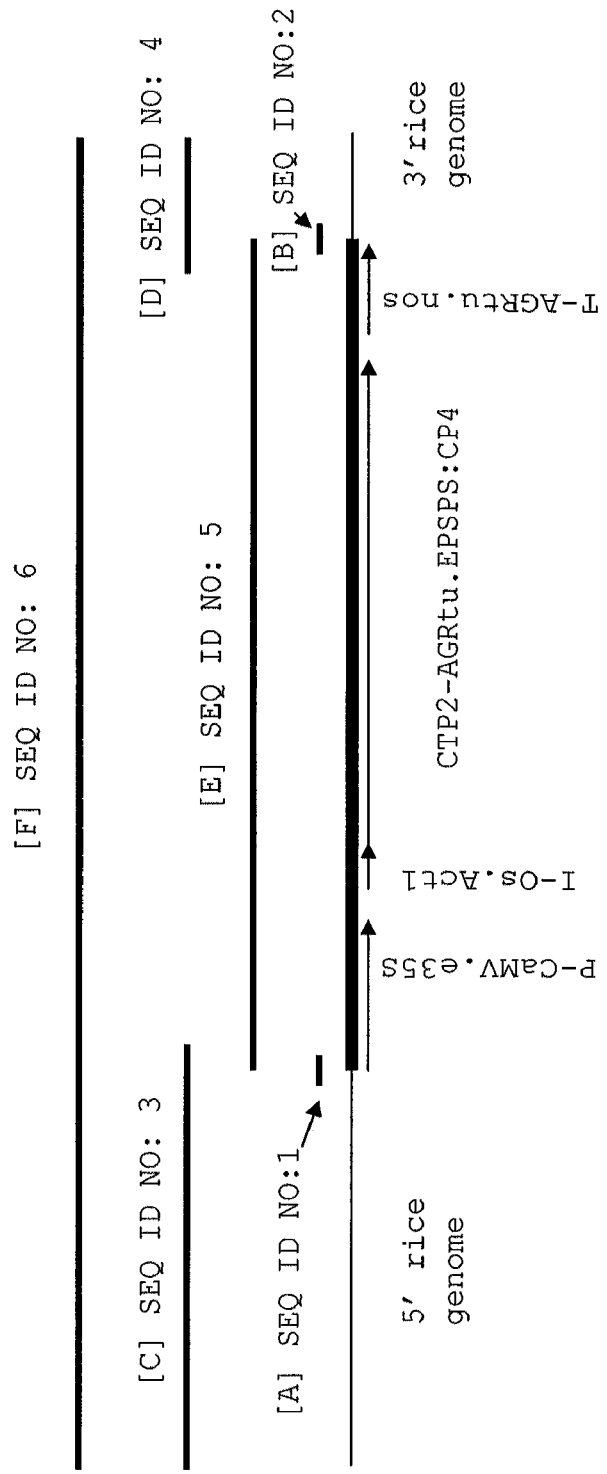

US 8,618,360 B2

RICE TRANSGENIC EVENT 17314 AND METHODS OF USE THEREOF

CROSS REFERENCE TO RELATED APPLICATIONS

This application claims the benefit of U.S. Provisional Application No. 61/164,895 filed Mar. 30, 2009, herein incorporated by reference in its entirety.

INCORPORATION OF SEQUENCE LISTING

The Sequence Listing, which is a part of the present disclosure, includes a computer readable 15 KB file entitled "MONS245WO_ST25.txt" comprising nucleotide and/or amino acid sequences of the present invention submitted via EFS-Web. The subject matter of the Sequence Listing is incorporated herein by reference in its entirety.

FIELD OF THE INVENTION

The present invention relates to transgenic rice event 17314. Plants comprising the event exhibit tolerance to glyphosate herbicide. The invention also relates to nucleic acid molecules, plants, plant parts, plant seeds, plant cells, agricultural products, and methods related to event 17314. The invention provides nucleotide molecules that are unique to the event and were created in connection with the insertion of transgenic DNA into the genome of a rice plant.

BACKGROUND OF THE INVENTION

Rice is an important crop in many areas of the world. The methods of biotechnology have been applied to rice in order to produce rice with improved traits. One such improved trait is herbicide tolerance. The expression of an herbicide tolerance transgene in a plant is useful for the purpose of producing a plant having the desirable characteristic of herbicide tolerance. The expression of a transgene in a plant may be influenced by the chromosomal location of the transgene, perhaps due to chromatin structure (e.g., heterochromatin), or the proximity of transcriptional regulatory elements (e.g., enhancers) close to the integration site. For this reason, it is often necessary to screen a large number of individual plant transformation events in order to identify an event having optimal expression of a transgene and therefore the specific desirable characteristic. For example, it has been observed in plants that there may be wide variation in the level of transgene expression among events. There may also be differences in spatial or temporal patterns of expression, e.g., differences in the relative transgene expression levels in various plant tissues, that may not correspond to the patterns expected from transcriptional regulatory elements present in the introduced gene construct. For this reason, it may be necessary to produce several hundred to several thousand different transgenic events and screen these for an event that has the desired transgene expression levels and patterns for commercial purposes. Such an event having the desired levels or patterns of transgene expression may then be used for introgressing the transgene into other genetic backgrounds by sexual crossing using plant breeding methods. Progeny of such crosses would have the transgene expression characteristics of the original transformant. This may be used to ensure reliable gene expression in a number of different varieties that are suitably adapted to specific local growing conditions.

SUMMARY OF THE INVENTION

The present invention provides transgenic rice plants comprising event 17314, which exhibit commercially acceptable tolerance to applications of glyphosate herbicide, having representative seed deposited with American Type Culture Collection (ATCC) with Accession No. PTA-9844. The invention also provides seeds, progeny, plant parts, cells, and commodity products of rice comprising event 17314. The invention also provides novel DNA molecules related to the genome of rice comprising event 17314 and methods of using these molecules. The invention also provides methods of using transgenic rice event 17314 and plants comprising the event and methods of producing glyphosate tolerant rice.

The present invention provides DNA molecules related to rice event 17314. These DNA molecules may comprise nucleotide sequences representing or derived from: the junction between the transgene insertion and flanking genomic DNA of rice event 17314, and/or a region of the genomic DNA flanking the inserted DNA, and/or a region of the integrated transgenic DNA flanking the insertion site, and/or a region of the integrated transgenic expression cassette, and/or a contiguous sequence of any of these regions. The present invention also provides DNA molecules useful as primers and probes diagnostic for rice event 17314. Rice plants, plant cells, plant parts, commodity products, progeny, and seeds comprising these molecules are also disclosed.

The present invention provides methods, compositions, and kits useful for detecting the presence of DNA derived from rice event 17314. The present invention provides a method for detection of event 17314 by contacting a sample comprising DNA with a primer set that when used in a nucleic acid amplification reaction with genomic DNA from rice event 17314 produces an amplified DNA diagnostic for rice event 17314, performing a nucleic acid amplification reaction thereby producing the amplified DNA, and detecting the amplified DNA. The present invention also provides a method for detection of event 17314 by contacting a sample comprising DNA with a probe that when used in a hybridization reaction with genomic DNA from event 17314 hybridizes to a DNA molecule specific for rice event 17314, performing a hybridization reaction, and detecting the hybridization of the probe to the DNA molecule. Kits comprising the methods and compositions of the present invention useful for detecting the presence of DNA derived from rice event 17314 are also provided.

The present invention provides a rice plant, seed, plant cell, progeny plant, plant part, or commodity product derived from a plant, plant cell, or seed comprising event 17314. The present invention also provides a rice plant, seed, plant cell, progeny plant, plant part, or commodity product comprising a DNA molecule having a nucleotide sequence selected from the group consisting of SEQ ID NO: 1-6, and complements and fragments thereof or a DNA molecule comprising at least 90% sequence identity to SEQ ID NO:6. The present invention also provides a rice plant, seed, plant cell, progeny plant, plant part, or commodity product derived from the plant or seed comprising event 17314 or comprising a DNA molecule that produces an amplified DNA molecule comprising SEQ ID NO: 1 and/or SEQ ID NO: 2, for instance in a DNA amplification method.

The present invention provides a method for controlling weeds in a field by planting rice comprising event 17314 and then applying an effective dose of glyphosate herbicide capable of controlling the weeds without injuring the plants comprising event 17314.

The present invention provides methods of producing a rice plant and/or seed that tolerates application of glyphosate herbicide by sexually crossing a rice plant comprising event 17314 or comprising SEQ ID NO: 1 or SEQ ID NO: 2 with a second rice plant, thereby producing seed, growing the seed to produce progeny plants, treating the progeny plants with glyphosate, and selecting a progeny plant that is tolerant to glyphosate. The methods may also include selfing the selected progeny plant to produce a plurality of second generation progeny plants and selecting from these a glyphosate tolerant plant. The methods may also include sexually crossing the selected progeny plant with another rice plant to produce seed, growing the seed to produce a second generation of progeny plants, treating the second generation of progeny plants with glyphosate, and selecting a second generation progeny plant that is tolerant to glyphosate. The present invention provides methods of producing a rice plant and/or seed that tolerates application of glyphosate herbicide by selfing a glyphosate tolerant plant comprising event 17314 and comprising SEQ ID NO: 1 or SEQ ID NO: 2, thereby producing seed, growing the seed to produce progeny plants, treating the progeny plants with glyphosate; and selecting a progeny plant that is tolerant to glyphosate.

The foregoing and other aspects of the invention will become more apparent from the following detailed description.

BRIEF DESCRIPTION OF THE DRAWINGS

FIG. 1. Diagrammatical representation of event 17314: [A] corresponds to the relative position of the 5' junction region (provide as SEQ ID NO: 1), which is the junction between the rice genome and the 5' portion of the inserted transgenic DNA; [B] corresponds to the relative position of the 3' junction region (provided as SEQ ID NO: 2), which is the junction between the rice genome and the 3' portion of the inserted transgenic DNA; [C] corresponds to the relative position of the 5' flanking region and a portion of the 5' end of the inserted transgenic DNA (provided as SEQ ID NO: 3), which includes the 5' rice genomic sequence flanking the integrated expression cassette of event 17314 and a region of the 5' end of the transgene DNA; [D] corresponds to the relative position of the 3' flanking region and a portion of the 3' end of the inserted transgenic DNA (provided as SEQ ID NO: 4), which includes the 3' rice genomic sequence flanking the integrated expression cassette of event 17314 and a region of the 3' end of the transgene DNA; [E] represents the transgene expression cassette inserted into the genome of the event 17314 (provided as SEQ ID NO: 5); and [F] represents the contiguous sequence of the flanking sequences and transgene expression cassette (provided SEQ ID NO: 6) comprising, as represented in the FIGURE from left to right, SEQ ID NO: 3, SEQ ID NO: 5 and SEQ ID NO: 4, in which SEQ ID NO: 1 and SEQ ID NO: 2 are incorporated as set forth above, as these sequences represent the junction sequences of event 17314.

BRIEF DESCRIPTION OF THE SEQUENCES

SEQ ID NO: 1—A twenty nucleotide sequence representing the 5' junction sequence between the rice genomic DNA and the integrated expression cassette. This nucleotide sequence corresponds to positions 283 through 302 of SEQ ID NO: 3 ([C], see FIG. 1) and to position 283 through 302 of SEQ ID NO: 6.

SEQ ID NO: 2—A twenty nucleotide sequence representing the 3' junction between the integrated expression cassette and the rice genomic DNA. This nucleotide sequence corresponds to positions 685 through 666 of SEQ ID NO: 4 ([D], see FIG. 1), and the reverse complement of SEQ ID NO: 2 corresponds to positions 3397 through 3416 of SEQ ID NO: 6.

SEQ ID NO: 3—The 5' sequence flanking the inserted DNA of event 17314 up to and including a region of transgenic DNA. Nucleotide positions 283 through 302 of SEQ ID NO: 3 correspond to nucleotide positions 1 through 20 of SEQ ID NO: 1 and nucleotide positions 293 through 302 of SEQ ID NO: 3 correspond to nucleotide positions 1 through 10 of SEQ ID NO:5.

SEQ ID NO: 4—The 3' sequence flanking the inserted DNA of event 17314 up to and including a region of transgene DNA insertion. Nucleotide position 666 through 685 of SEQ ID NO: 4 correspond to nucleotide position 1 through 20 of SEQ ID NO:2, and the reverse complement strand of nucleotide positions 666 through 685 of SEQ ID NO: 4 corresponds to nucleotide positions 3105 through 3114 of SEQ ID NO: 5.

SEQ ID NO: 5—The sequence of the integrated expression cassette conferring glyphosate herbicide tolerance. SEQ ID NO: 5 corresponds to nucleotide positions 293 through 3046 of SEQ ID NO: 6.

SEQ ID NO: 6—A nucleotide sequence representing the contig of the 5' sequence flanking the inserted DNA of event 17314 (SEQ ID NO: 3), the sequence of the integrated expression cassette (SEQ ID NO: 5), and the 3' sequence flanking the inserted DNA of event 17314 (reverse complement of SEQ ID NO: 4).

SEQ ID NO: 7—Primer SQ4183, used to identify event 17314. Primer SQ4183 is complementary to the genomic region flanking the 5' region of the inserted expression cassette, close to the right transgene DNA insertion border. An amplicon produced using the combination of primers SQ4183 and SQ4191 (SEQ ID NO: 8) indicates the presence of event 17314.

SEQ ID NO: 8—Primer SQ4191, used to identify event 17314. Primer SQ4191 is complementary to the 5' region of the inserted expression cassette, close to the transgene DNA insertion border. An amplicon produced using the combination of primers SQ4183 (SEQ ID NO: 7) and SQ4191 indicates the presence of event 17314.

SEQ ID NO: 9—Probe PB1491, used to identify event 17314 and is complementary to a fragment of the 5' junction sequence. The probe may be linked to a detectable label, such as a 6FAM™. Release of a fluorescent signal in a TAQMAN® (PE Applied Biosystems, Foster City, Calif.) assay using primers, such as SQ4183 and SQ4191, in combination with a probe, such as 6FAM™-labeled probe PB1491, is diagnostic for the presence of event 17314.

SEQ ID NO: 10—Primer SQ1875, used to identify event 17314. Primer SQ1875 is complementary to the 3' region of the inserted expression cassette, close to the transgene DNA insertion border. An amplicon produced using the combination of primers SQ1875 and SQ3628 (SEQ ID NO: 11) indicates the presence of event 17314.

SEQ ID NO: 11—Primer SQ3628, used to identify event 17314. Primer SQ3628 is complementary to the genomic region flanking the 3' end of the inserted expression cassette, close to the transgene DNA insertion border. An amplicon produced using the combination of primers SQ1875 (SEQ ID NO: 10) and SQ3628 indicates the presence of event 17314.

SEQ ID NO: 12—Primer SQ1871, used to identify event 17314 flanking genomic DNA. Primer SQ1871 is complementary to the 5' region of the inserted expression cassette, close to the transgene DNA insertion border.

SEQ ID NO: 13—Primer SQ1869, used to identify event 17314 flanking genomic DNA. Primer SQ1869 is complementary to the 5' region of the inserted expression cassette, close to the transgene DNA insertion border.

SEQ ID NO: 14—Primer SQ1880, used to identify event 17314 flanking genomic DNA. Primer SQ1880 is complementary to the 3' region of the inserted expression cassette, close to the transgene DNA insertion border.

SEQ ID NO: 15—Primer SQ3629, used to identify event 17314 flanking genomic DNA. Primer SQ3626 is complementary to the genomic region flanking the 5' end of the inserted expression cassette, close to the transgene DNA insertion border.

SEQ ID NO: 16—Primer SQ3627, used to identify event 17314 flanking genomic DNA. Primer SQ3626 is complementary to the genomic region flanking the 3' end of the inserted expression cassette, close to the transgene DNA insertion border.

DETAILED DESCRIPTION

The following definitions and methods are provided to better define the present invention and to guide those of ordinary skill in the art in the practice of the present invention. Unless otherwise noted, terms are to be understood according to conventional usage by those of ordinary skill in the relevant art.

As used herein, the term "comprising" means "including but not limited to".

The present invention provides event 17314 and transgenic rice plants comprising event 17314 that exhibit commercially acceptable tolerance to applications of glyphosate herbicide. The event comprises a single insertion of transgenic DNA into the chromosome/genome of the rice germplasm. An event comprising plant can be produced by: (i) transformation of a plant cell with a nucleic acid construct that includes a transgene of interest, (ii) regeneration of a population of plants resulting from the insertion of the transgene into the genome of the plant, and (iii) selection of a particular plant characterized by insertion of the transgene into a particular location in the plant's genome. The term "event" refers to a specific transgenic insertion of a gene of interest into a particular location in the genome. A plant comprising the event can refer to the original transformant that includes the transgene inserted into the particular location in the plant's genome. A plant comprising the event can also refer to progeny of the transformant that include the transgene inserted into the particular location in the plant's genome. Such progeny may be produced by a sexual outcross between the transformant, or its progeny, and another plant. Such other plant may be a transgenic plant comprising the same or different transgene and/or a nontransgenic plant, such as one from a different variety. Even after repeated back-crossing to a recurrent parent, the inserted DNA and flanking DNA from the transformed parent is present in the progeny of the cross at the same genomic location.

As used herein, the term "rice" means *Oryza sativa* and includes all plant varieties that can be bred with rice, including wild rice species as well as those plants belonging to the genus *Oryza* that permit breeding between species.

The term "event" also refers to a DNA molecule from the original transformant comprising the inserted DNA and the flanking rice genomic DNA immediately adjacent to either side of the inserted DNA. This DNA molecule is created by the act of inserting the transgenic DNA into the genome of the rice plant, i.e., by the act of transformation. This DNA molecule therefore comprises a nucleotide sequence that is both specific to the event and that is unique to the genome of the rice plant into which the transgenic DNA has been inserted, in that this nucleotide sequence contains both the sequence of a particular region of rice genomic DNA and of the transgenic DNA insert. The arrangement of the inserted DNA in event 17314 in relation to the surrounding rice plant genome DNA is therefore specific and unique to event 17314. This DNA molecule is also an integral part of the rice chromosome of the plant that comprises event 17314 and as such is static in the plant and may be passed on to progeny of the plant.

Event 17314 confers tolerance to glyphosate herbicide applied to the rice plant. "Glyphosate" refers to N-phosphonomethyl-glycine and its salts. N-phosphonomethyl-glycine is an herbicide that has activity on a broad spectrum of plant species. When applied to a plant surface, glyphosate moves systemically through the plant. Glyphosate is phytotoxic due to its inhibition of the shikimic acid pathway, which provides a precursor for the synthesis of aromatic amino acids.

As used herein, the term "recombinant" refers to a form of DNA and/or protein and/or an organism that would not normally be found in nature and as such was created by human intervention. Such human intervention may produce a recombinant DNA molecule and/or a recombinant plant. As used herein, a "recombinant DNA molecule" is a DNA molecule comprising a combination of DNA molecules that would not naturally occur together and is the result of human intervention, e.g., a DNA molecule that is comprised of a combination of at least two DNA molecules heterologous to each other, and/or a DNA molecule that is artificially synthesized and comprises a polynucleotide sequence that deviates from the polynucleotide sequence that would normally exist in nature, and/or a DNA molecule that comprises a transgene artificially incorporated into a host cell's genomic DNA and the associated flanking DNA of the host cell's genome. An example of a recombinant DNA molecule is a DNA molecule described herein resulting from the insertion of the transgene into the rice genome, which may ultimately result in the expression of a recombinant RNA and/or protein molecule in that organism. As used herein, a "recombinant plant" is a plant that would not normally exist in nature, is the result of human intervention, and contains a transgene and/or heterologous DNA molecule incorporated into its genome. As a result of such genomic alteration, the recombinant plant is distinctly different from the related wildtype plant. An example of a recombinant plant is a rice plant described herein as comprising event 17314.

As used herein, the term "transgene" refers to a polynucleotide molecule artificially incorporated into a host cell's genome. Such transgene may be heterologous to the host cell. The term "transgenic plant" refers to a plant comprising such a transgene.

As used herein, the term "heterologous" refers to a first molecule not normally found in combination with a second molecule in nature. For example, a molecule may be derived from a first species and inserted into the genome of a second species. The molecule would thus be heterologous to the host and artificially incorporated into a host cell's genome.

As used herein, the term "chimeric" refers to a single DNA molecule produced by fusing a first DNA molecule to a second DNA molecule, where neither first nor second DNA molecule would normally be found in that configuration, i.e., fused to the other. The chimeric DNA molecule is thus a new DNA molecule not otherwise normally found in nature.

The present invention provides DNA molecules and their corresponding nucleotide sequences. As used herein, the term "DNA", "DNA molecule", "polynucleotide molecule" refers to a double-stranded DNA molecule of genomic or synthetic origin, i.e., a polymer of deoxyribonucleotide bases or a polynucleotide molecule, read from the 5' (upstream) end to the 3' (downstream) end. As used herein, the term "DNA sequence", "nucleotide sequence" or "polynucleotide sequence" refers to the nucleotide sequence of a DNA molecule. The nomenclature used herein is that required by Title 37 of the United States Code of Federal Regulations §1.822 and set forth in the tables in WIPO Standard ST.25 (1998), Appendix 2, Tables 1 and 3. The present invention is disclosed with reference to only one strand of the two nucleotide sequence strands that are present in the genome of the transgenic event 17314 at the position of the inserted transgenic DNA, particularly with reference to SEQ ID NOs: 1-6. Therefore, by implication and derivation, the complementary sequences, also referred to in the art as the complete complement or the reverse complementary sequences, are within the scope of the present invention and are therefore also intended to be within the scope of the subject matter claimed.

The nucleotide sequence corresponding to the complete nucleotide sequence of the inserted transgenic DNA and substantial segments of the rice genomic DNA flanking either end of the inserted transgenic DNA is provided herein as SEQ ID NO: 6. A subsection of this is the inserted transgenic DNA provided as SEQ ID NO: 5. The nucleotide sequence of the rice genomic DNA physically linked by phosphodiester bond linkage to and therefore flanking the 5' end of the inserted transgenic DNA (SEQ ID NO: 5) is set forth as shown in SEQ ID NO: 3. The nucleotide sequence of the rice genome DNA physically linked by phosphodiester bond linkage to and therefore flanking the 3' end of the inserted transgenic DNA (SEQ ID NO: 5) is set forth as shown in SEQ ID NO: 4.

Event 17314 further comprises two polynucleotide sequences, one spanning the 5' location and one spanning the 3' location where the transgenic DNA is inserted into the genomic DNA, referred to herein as the junction sequences. A "junction sequence" or "junction region" refers to a DNA sequence and/or corresponding DNA molecule that spans both the inserted transgenic DNA and the adjacent flanking genomic DNA. The junction sequences are arbitrarily represented by two 20 nucleotide sequences and provided as SEQ ID NO: 1 and SEQ ID NO: 2, each representing 10 nucleotides of the immediately adjacent flanking genomic DNA joined to 10 nucleotides of insert DNA. These nucleotides are connected by phosphodiester linkage. In rice, SEQ ID NO: 1 and SEQ ID NO: 2 do not naturally occur in the genome and are specific and unique to transgenic event 17314, and the identification of these sequences, or at least about 11, at least about 13, or at least about 15 contiguous nucleotides of each of these sequences, in any nucleotide sequence derived from a rice plant, is conclusive that the DNA was obtained from rice event 17314, and is diagnostic for the presence in a sample of DNA from rice event 17314. SEQ ID NO: 1 is a 20 nucleotide sequence spanning the junction between the rice genomic DNA and the 5' end of the inserted DNA. SEQ ID NO: 2 is a 20 nucleotide sequence spanning the junction between the rice genomic DNA and the 3' end of the inserted DNA. The present invention thus provides a DNA molecule that contains at least the nucleotide sequence as set forth in either or both of SEQ ID NO: 1 and SEQ ID NO: 2. Any segment of DNA derived from transgenic rice event 17314 that is sufficient to include at least about 11, at least about 13, or at least about 15 contiguous nucleotides of SEQ ID NO: 1 is within the scope of the present invention. Any segment of DNA derived from transgenic rice event 17314 that is sufficient to include at least about 11, at least about 13, or at least about 15 contiguous nucleotides of SEQ ID NO: 2 is within the scope of the present invention. In addition, any polynucleotide comprising a sequence complementary to any of the sequences described within this paragraph is within the scope of the present invention. FIG. 1 illustrates the physical arrangement of SEQ ID NO: 1-5 relative to SEQ ID NO: 6 arranged from 5' to 3'. The present invention also provides a nucleic acid molecule comprising at least 80%, 85%, 90%, 95%, 97%, 98% or 99% of SEQ ID NO:6.

The present invention provides exemplary DNA molecules that can be used either as primers or probes for diagnosing the presence of DNA derived from event 17314 in a sample. Such primers or probes are specific for a target nucleic acid sequence and as such are useful for the identification of rice event 17314 by the methods of the invention described herein.

A "primer" is typically a highly purified, isolated polynucleotide that is designed for use in specific annealing or hybridization methods that involve thermal amplification. A pair of primers may be used with template DNA, such as a sample of rice genomic DNA, in a thermal amplification, such as polymerase chain reaction (PCR), to produce an amplicon, where the amplicon produced from such reaction would have a DNA sequence corresponding to sequence of the template DNA located between the two sites where the primers hybridized to the template. As used herein, an "amplicon" is a piece or fragment of DNA that has been synthesized using amplification techniques. In one embodiment of the invention, an amplicon diagnostic for event 17314 comprises a sequence not naturally found in the rice genome. An amplicon of the present invention comprises at least about 11 contiguous nucleotides, at least about 13 contiguous nucleotides, or at least about 11, at least about 13, or at least about 15 contiguous nucleotides of SEQ ID NO: 1, SEQ ID NO: 2, and/or complements thereof. A primer is typically designed to hybridize to a complementary target DNA strand to form a hybrid between the primer and the target DNA strand, and the presence of the primer is a point of recognition by a polymerase to begin extension of the primer (i.e., polymerization of additional nucleotides into a lengthening polynucleotide molecule) using as a template the target DNA strand. Primer pairs, as used in the present invention, are intended to refer to use of two primers binding opposite strands of a double stranded nucleotide segment for the purpose of amplifying linearly the polynucleotide segment between the positions targeted for binding by the individual members of the primer pair, typically in a thermal amplification reaction or other conventional nucleic-acid amplification methods. Exemplary DNA molecules useful as primers are provided as SEQ ID NO: 7-8 and 10-11. A primer pair provided as SEQ ID NO: 7 and SEQ ID NO: 8, are provided as a first DNA molecule and a second DNA molecule that is different from the first DNA molecule, and both molecules are each of sufficient length of contiguous nucleotides of either SEQ ID NO: 3, SEQ ID NO: 5, or SEQ ID NO: 6 or the complements thereof to function as DNA primers that, when used together in a thermal amplification reaction with template DNA derived from rice event 17314, produce an amplicon comprising at least about 11 contiguous nucleotides, at least about 13 contiguous nucleotides, or at least about 11, at least about 13, or at least about 15 contiguous nucleotides of SEQ ID NO: 1. An exemplary pair of DNA molecules is provided, i.e., SEQ ID NO: 10 and SEQ ID NO: 11, as a first DNA molecule and a second DNA molecule that is different from the first DNA molecule, and both molecules are each of sufficient length of contiguous nucleotides of either SEQ ID NO: 4, SEQ ID NO: 5, or SEQ ID NO: 6 or the complements thereof to function as DNA primers that, when used together in a thermal amplification reaction with template DNA derived from rice event 17314, produce an amplicon at least about 11 contiguous nucleotides, at least about 13 contiguous nucleotides, or at least about 11, at least about 13, or at least about 15 contiguous nucleotides of SEQ ID NO: 2.

A "probe" is an isolated nucleic acid that is complementary to a strand of a target nucleic acid. Probes according to the present invention include not only deoxyribonucleic or ribonucleic acids but also polyamides and other probe materials that bind specifically to a target DNA sequence and the detection of such binding can be useful in diagnosing, discriminating, determining, or confirming the presence of that target DNA sequence in a particular sample. A probe may be attached to a conventional detectable label or reporter molecule, e.g., a radioactive isotope, ligand, chemiluminescent agent, or enzyme. In one embodiment of the invention, a probe diagnostic for event 17314 comprises a sequence not naturally found in the rice genome. An exemplary DNA molecule useful as a probe is provided as SEQ ID NO: 9.

Probes and primers according to the present invention may have complete sequence identity with the target sequence, although primers and probes differing from the target sequence that retain the ability to hybridize preferentially to target sequences may be designed by conventional methods. In order for a nucleic acid molecule to serve as a primer or probe it need only be sufficiently complementary in sequence to be able to form a stable double-stranded structure under the particular solvent and salt concentrations employed. Any conventional nucleic acid hybridization or amplification method can be used to identify the presence of transgenic DNA from rice event 17314 in a sample. Probes and primers are generally at least about 11 nucleotides, at least about 18 nucleotides, at least about 24 nucleotides, or at least about 30 nucleotides or more in length. Such probes and primers hybridize specifically to a target DNA sequence under stringent hybridization conditions. Conventional stringency conditions are described by Sambrook et al., 1989, and by Haymes et al., In: *Nucleic Acid Hybridization, a Practical Approach*, IRL Press, Washington, D.C. (1985). As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Departures from complete complementarity are therefore permissible, as long as such departures do not completely preclude the capacity of the molecules to form a double-stranded structure.

As used herein, the term "isolated" refers to at least partially separating a molecule from other molecules normally associated with it in its native or natural state. In one embodiment, the term "isolated" refers to a DNA molecule that is at least partially separated from the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated even when integrated into the chromosome of a host cell or present in a nucleic acid solution with other DNA molecules.

Any number of methods well known to those skilled in the art can be used to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

The DNA molecules and corresponding nucleotide sequences provided herein are therefore useful for, among other things, identifying rice event 17314, selecting plant varieties or hybrids comprising rice event 17314, detecting the presence of DNA derived from rice event 17314 in a sample, and monitoring samples for the presence and/or absence of rice event 17314 or plants and plant parts comprising rice event 17314.

The present invention provides rice plants, progeny, seeds, plant cells, plant parts (such as pollen, ovule, pod, flower, root or stem tissue, fibers, and leaves), and commodity products. These plants, progeny, seeds, plant cells, plant parts, and commodity products contain a detectable amount of a polynucleotide of the present invention, i.e., such as a polynucleotide having at least one of the sequences provided as SEQ ID NO: 1 and SEQ ID NO: 2. Plants, progeny, seeds, plant cells, and plant parts of the present invention may also contain one or more additional transgenes. Such transgene may be any nucleotide sequence encoding a protein or RNA molecule conferring a desirable trait including but not limited to increased insect resistance, increased water use efficiency, increased yield performance, increased drought resistance, increased seed quality, improved nutritional quality, and/or increased herbicide tolerance, in which the desirable trait is measured with respect to a rice plant lacking such additional transgene.

The present invention provides rice plants, progeny, seeds, plant cells, and plant part such as pollen, ovule, pod, flower, root or stem tissue, and leaves derived from a transgenic rice plant comprising event 17314. A representative sample of seed comprising event 17314 has been deposited according to the Budapest Treaty for the purpose of enabling the present invention. The repository selected for receiving the deposit is the American Type Culture Collection (ATCC) having an address at 10801 University Boulevard, Manassas, Va. USA, Zip Code 20110. The ATCC repository has assigned the accession No. PTA-9844 to the event 17314 seed.

The present invention provides a microorganism comprising a DNA molecule having SEQ ID NO: 1 and SEQ ID NO: 2 present in its genome. An example of such a microorganism is a transgenic plant cell. Microorganisms, such as a plant cell of the present invention, are useful in many industrial applications, including but not limited to: (i) use as research tool for scientific inquiry or industrial research; (ii) use in culture for producing endogenous or recombinant carbohydrate, lipid, nucleic acid, or protein products or small molecules that may be used for subsequent scientific research or as industrial products; and (iii) use with modern plant tissue culture techniques to produce transgenic plants or plant tissue cultures that may then be used for agricultural research or production. The production and use of microorganisms such as transgenic plant cells utilizes modern microbiological techniques and human intervention to produce a man-made, unique microorganism. In this process, recombinant DNA is inserted into a plant cell's genome to create a transgenic plant cell that is separate and unique from naturally occurring plant cells. This transgenic plant cell can then be cultured much like bacteria and yeast cells using modern microbiology techniques and may exist in an undifferentiated, unicellular state. The new plant cell's genetic composition and phenotype is a technical effect created by the integration of the heterologous DNA into the genome of the cell. Another aspect of the present invention is a method of using a microorganism of the present invention. Methods of using microorganisms of the present invention, such as transgenic plant cells, include (i) methods of producing transgenic cells by integrating recombinant DNA into genome of the cell and then using this cell to derive additional cells possessing the same heterologous DNA; (ii) methods of culturing cells that contain recombinant DNA using modern microbiology techniques; (iii) methods of producing and purifying endogenous or recombinant carbohydrate, lipid, nucleic acid, or protein products from cultured cells; and (iv) methods of using modern plant tissue culture techniques with transgenic plant cells to produce transgenic plants or transgenic plant tissue cultures.

Plants of the present invention may pass along the event DNA, including the transgene, to progeny. As used herein, "progeny" includes any plant, seed, plant cell, and/or regenerable plant part comprising the event DNA derived from an ancestor plant and/or a polynucleotide having at least one of the sequences provided as SEQ ID NO: 1 and SEQ ID NO: 2. Plants, progeny, and seeds may be homozygous or heterozygous for the transgene. Progeny may be grown from seeds produced by a plant comprising event 17314 and/or from seeds produced by a plant fertilized with pollen from a plant comprising event 17314.

Progeny plants may be self-pollinated (also known as "selfing") to generate a true breeding line of plants, i.e., plants homozygous for the transgene. Selfing of appropriate progeny can produce plants that are homozygous for both added, exogenous genes.

Alternatively, progeny plants may be outcrossed, e.g., bred with another unrelated plant, to produce a varietal or a hybrid seed or plant. The other unrelated plant may be transgenic or nontransgenic. A varietal or hybrid seed or plant of the present invention may thus be derived by crossing a first parent that lacks the specific and unique DNA of the rice event 17314 with a second parent comprising rice event 17314, resulting in a hybrid comprising the specific and unique DNA of event 17314. Each parent can be a hybrid or an inbred/varietal, so long as the cross or breeding results in a plant or seed of the present invention, i.e., a seed having at least one allele containing the specific and unique DNA of event 17314 comprising SEQ ID NO: 1 and SEQ ID NO: 2. Two different transgenic plants may thus be mated to produce hybrid offspring that contain two independently segregating, added, exogenous genes. For example, the glyphosate tolerant rice comprising event 17314 can be crossed with other transgenic rice plant to produce a plant having the characteristics of both transgenic parents. One example of this would be a cross of glyphosate tolerant rice comprising event 17314 with a rice plant having one or more additional traits resulting in a progeny plant or seed that is tolerant to glyphosate and has one or more additional traits. For example, rice plants exhibiting tolerance to phosphinothricin or glufosinate herbicide could be crossed with rice plants comprising event 17314 to produce a progeny plant or seed that is tolerant to glyphosate and phosphinothricin or glufosinate herbicide. The plants and seeds used in the methods disclosed herein may thus also contain one or more additional transgenes. Such transgene may be any nucleotide sequence encoding a protein or RNA molecule conferring a desirable trait including but not limited to increased insect resistance, increased water use efficiency, increased yield performance, increased drought resistance, increased seed quality, improved nutritional quality, improved stress tolerance, and/or increased herbicide tolerance, in which the desirable trait is measured with respect to a rice plant lacking such additional transgene.

Herbicides for which transgenic plant tolerance has been demonstrated and the method of the present invention can be applied, include but are not limited to: glyphosate, glufosinate, sulfonylureas, imidazolinones, bromoxynil, delapon, cyclohexanedione, protoporphyrionogen oxidase inhibitors, and isoxasflutole herbicides. Polynucleotide molecules encoding proteins involved in herbicide tolerance are known in the art and include, but are not limited to, a polynucleotide molecule encoding: glyphosate-tolerant 5-enolpyruvylshikimate-3-phosphate synthase (EPSPS) (see, for example, U.S. Pat. Nos. 5,627,061; 5,633,435; 6,040,497; 5,094,945; 5,804,425; 6,248,876; 7,183,110; RE39,247); glyphosate oxidoreductase (GOX) (see, for example, U.S. Pat. No. 5,776,760); glyphosate-n-acetyltransferase (GAT); an herbicide-tolerant acetolactate synthase (ALS, also known as acetohydroxyacid synthase (AHAS)) for tolerance to sulfonylureas, imidazolinones, triazolopyrimidines, pyrimidinyl oxybenzoates, sulfonylamino carbonyl triazolinones, and/or heteroaryl ethers; an herbicide-tolerant acetyl coenzyme A carboxylase (ACCase) or R-2,4-dichlorophenoxypropionate dioxygenase (rdpA) for tolerance to an aryloxyphenoxypropionate (AOPP) (such as haloxyfop, quizalofop, dichlorofop, and diclofop); a detoxification protein such as a 2,4-D dioxygenase (tfdA), R-2,4-dichlorophenoxypropionate dioxygenase (rdpA), AryloxyAlkanoate Dioxygenase (AAD), and/or S-2,4-dichorprop dioxygenase (sdpA) for tolerance to synthetic auxin herbicides; a bromoxynil nitrilase (Bxn) for Bromoxynil tolerance (see, for example, U.S. Pat. No. 4,810,648); a phytoene desaturase (crtI) for tolerance to norflurazon; the bialaphos resistance (bar) or phosphinothricin acetyltransferase (PAT) protein (see, for example, U.S. Pat. Nos. 5,646,024 and 5,276,268) for tolerance to glufosinate and bialaphos; and a protein for triketone (mezotrione, tembotrione, topromezone, isoxazole) herbicide-tolerance such as tolerant 4-HydroxyPhenylPyruvate Dioxygenase (HPPD), a detoxifying cytochrome P450, or an HPPD pathway bypass such as *Artbrobacter globiformis* HPP oxidase (HPPO) and *Pseudomonas acidovorans* 4-HPA 1-hydroxylase (HPAH) and NADH oxidoreductase (HPAC).

Polynucleotide molecules encoding other proteins useful in transgenic plants are known in the art and include, but are not limited to, a polynucleotide molecule encoding: *E. coli* cspA (PCT Publication No. WO2005/033318); *B. subtilis* cspB (PCT Publication No. WO2005/033318); *Zea mays* Mg transporter (U.S. Publication Nos. 20040034888; 20070011783; 20070294782); *Zea mays* nfb2 (a.k.a hap3) (U.S. Publication Nos. 20050022266 and 20080104730; PCT Publication No. WO2008/002480); cotton csp-like (U.S. Ser. No. 11/980,758; U.S. Publication No. 20050097640; PCT Publication No. WO 2005/033318); wheat csp-like (U.S. Pat. No. 7,214,786; U.S. Publication No. 20050097640); G1988 (U.S. Ser. No. 09/474,435; PCT Publication No. WO04/031349); G1073 (U.S. Pat. No. 6,717,034 and U.S. Publication No. 20050097631); G1274 (U.S. Publication No. 20090265813); and CGPG 2117 (U.S. Publication No. 20080090998). Other polynucleotide molecules encoding proteins useful in transgenic plants are known in the art and include those useful for pest control such as nematicidal agents, fungicidal agents, and insecticidal agents. Insecticidal agents include, but are not limited to, Bt toxins and/or toxins from *Xenhorabdus, Photorhabdus, Bacillus* (such as *Bacillus laterosporous*), *Serratia, Klebsiella, Erwinia*, and the like. Bt toxins include but are not limited to VIP toxins, Cry1's, Cry2's, Cry3's, Cry4's, Cry5's, Cry7's, Cry8's, Cry9's, and binary insecticidal toxins such as those derived from Bt, and the like.

Back-crossing to a parental plant and out-crossing with a non-transgenic plant are also contemplated, as is vegetative propagation. Descriptions of other breeding methods that are commonly used for different traits and crops can be found in one of several references, e.g., Fehr, in Breeding Methods for Cultivar Development, Wilcox J. ed., American Society of Agronomy, Madison Wis. (1987).

The present invention provides a plant part that is derived from rice plants comprising event 17314. As used herein, a "plant part" refers to any part of a plant which is comprised of material derived from a rice plant comprising event 17314. Plant parts include but are not limited to pollen, ovule, pod, flower, root or stem tissue, fibers, and leaves. Plant parts may be viable, nonviable, regenerable, and/or nonregenerable.

The present invention provides a commodity product that is derived from rice plants comprising event 17314. As used herein, a "commodity product" refers to any composition or product which is comprised of material derived from a rice plant, seed, plant cell, or plant part comprising event 17314. Commodity products may be sold to consumers and may be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animals consumption, oil, meal, flour, flakes, bran, fiber, milk, cheese, paper, cream, wine, and any other food for human consumption; and biomasses and fuel products. Viable commodity products include but are not limited to seeds and plant cells. Rice plants comprising event 17314 can thus be used to manufacture any commodity product typically acquired from rice. Any such commodity product that is derived from plants comprising event 17314 may contain at least a detectable amount of the specific and unique DNA corresponding to event 17314, and specifically may contain a detectable amount of a polynucleotide containing at least 15 contiguous nucleotides of SEQ ID NO: 1 or SEQ ID NO: 2. Any standard method of detection for polynucleotide molecules may be used, including methods of detection disclosed herein. A commodity product is within the scope of the present invention if there is any detectable amount of SEQ ID NO: 1 or SEQ ID NO: 2 in the commodity product.

The plants, progeny, seeds, plant cells, plant parts (such as pollen, ovule, pod, flower, root or stem tissue, and leaves), and commodity products of the present invention are therefore useful for, among other things, growing plants for the purpose of producing seed and/or plant parts comprising event 17314 for agricultural purposes, producing progeny comprising event 17314 for plant breeding and research purposes, use with microbiological techniques for industrial and research applications, and sale to consumers.

The present invention provides methods for controlling weeds and methods for producing plants using glyphosate herbicide and plants comprising event 17314. A method for controlling weeds in a field is provided and consists of planting varietal or hybrid plants comprising event 17314 in a field and applying a herbicidally effective dose of glyphosate to the field for the purpose of controlling weeds in the field without injuring the plants comprising event 17314. Such application of glyphosate herbicide may be pre-emergence, i.e., any time after seed comprising event 17314 is planted and before plants comprising event 17314 emerge, or post-emergence, i.e., any time after plants comprising event 17314 emerge. Another method for controlling weeds in a field is also provided and consists of applying an effective dose of glyphosate herbicide to control weeds in a field and then planting rice comprising event 17314 in the field. Such application of glyphosate herbicide would be pre-planting, i.e., before seed comprising event 17314 is planted, and could be done any time pre-planting including, but not limited to, about 14 days pre-planting to about 1 day pre-planting. An herbicidally effective dose of glyphosate for use in the field should consist of a range from about 0.5 pounds of glyphosate per acre to as much as about 4.5 pounds of glyphosate per acre over a growing season. Multiple applications of glyphosate may be used over a growing season, for example, two applications (such as a pre-planting application and a post-emergence application or a pre-emergence application and a post-emergence application) or three applications (such as a pre-planting application, a pre-emergence application, and a post-emergence application).

Methods for producing an herbicide tolerant rice plant comprising the DNA sequences specific and unique to the transgenic event 17314 of the present invention are provided. Transgenic plants used in these methods may be homozygous or heterozygous for the transgene. Progeny plants produced by these methods may be varietal or hybrid plants; may be grown from seeds produced by a plant and/or from seed comprising event 17314 produced by a plant fertilized with pollen from a plant comprising event 17314; and may be homozygous or heterozygous for the transgene. Progeny plants may be subsequently self-pollinated to generate a true breeding line of plants, i.e., plants homozygous for the transgene, or alternatively may be outcrossed, e.g., bred with another unrelated plant, to produce a varietal or a hybrid seed or plant.

A rice plant that tolerates application of glyphosate herbicide may be produced by sexually crossing a plant comprising event 17314 comprising a polynucleotide molecule comprising the sequence of SEQ ID NO: 1 and SEQ ID NO: 2 with another rice plant and thereby producing seed, which is then grown into progeny plants. These progeny plants may then be treated with glyphosate herbicide to select for progeny plants that are tolerant to glyphosate herbicide. Alternatively, these progeny plants may be analyzed using diagnostic methods to select for progeny plants that contain the event 17314 DNA. The other plant used in the crossing may or may not be tolerant to glyphosate herbicide and may or may not be transgenic. The progeny plant and/or seed produced may be varietal or hybrid seed.

In practicing this method, the step of sexually crossing one plant with another plant, i.e., cross-pollinating, may be accomplished or facilitated by human intervention, for example: by human hands collecting the pollen of one plant and contacting this pollen with the style or stigma of a second plant; by human hands and/or actions removing, destroying, or covering the stamen or anthers of a plant (e.g., by detasseling or by application of a chemical gametocide) so that natural self-pollination is prevented and cross-pollination would have to take place in order for fertilization to occur; by human placement of pollinating insects in a position for "directed pollination" (e.g., by placing beehives in orchards or fields or by caging plants with pollinating insects); by human opening or removing of parts of the flower to allow for placement or contact of foreign pollen on the style or stigma (e.g., in rice which naturally has flowers that hinder or prevent cross-pollination, making them naturally obligate self-pollinators without human intervention); by selective placement of plants (e.g., intentionally planting plants in pollinating proximity); and/or by application of chemicals to precipitate flowering or to foster receptivity (of the stigma for pollen).

A rice plant that tolerates application of glyphosate herbicide may be produced by selfing a plant comprising event 17314 comprising a polynucleotide molecule comprising the sequence of SEQ ID NO: 1 and SEQ ID NO: 2 and thereby producing seed, which is then grown into progeny plants. These progeny plants may then be treated with glyphosate herbicide to select for progeny plants that are tolerant to glyphosate herbicide. Alternatively, these progeny plants may be analyzed using diagnostic methods to select for progeny plants that contain the event 17314 DNA.

In practicing this method, the step of sexually crossing one plant with itself, i.e., self-pollinating or selfing, may be accomplished or facilitated by human intervention, for example: by human hands collecting the pollen of the plant and contacting this pollen with the style or stigma of the same plant and then optionally preventing further fertilization of the plant; by human hands and/or actions removing, destroying, or covering the stamen or anthers of other nearby plants (e.g., by detasseling or by application of a chemical gametocide) so that natural cross-pollination is prevented and self-pollination would have to take place in order for fertilization to occur; by human placement of pollinating insects in a position for "directed pollination" (e.g., by caging a plant alone with pollinating insects); by human manipulation of the flower or its parts to allow for self-pollination; by selective placement of plants (e.g., intentionally planting plants beyond pollinating proximity); and/or by application of chemicals to precipitate flowering or to foster receptivity (of the stigma for pollen).

Progeny rice plants and seeds encompassed by these methods and produced by using these methods will be distinct from other rice plants, for example because the progeny rice plants and seeds: are recombinant and as such created by human intervention; are glyphosate herbicide tolerant; contain at least one allele that consists of the transgene DNA of the present invention; and/or contain a detectable amount of a polynucleotide sequence selected from the group consisting of SEQ ID NO: 1 and SEQ ID NO: 2. A seed may be selected from an individual progeny plant, and so long as the seed comprises SEQ ID NO: 1 and SEQ ID NO: 2, it will be within the scope of the present invention.

In practicing the present invention, two different transgenic plants can be crossed to produce hybrid offspring that contain two independently segregating heterologous genes. Selfing of appropriate progeny can produce plants that are homozygous for both genes. Back-crossing to a parental plant and out-crossing with a non-transgenic plant are also contemplated, as is vegetative propagation. Descriptions of other methods that are commonly used for different traits and crops can be found in one of several references, e.g., Fehr, in Breeding Methods for Cultivar Development, Wilcox J. ed., American Society of Agronomy, Madison Wis. (1987).

The plants and seeds used in the methods disclosed herein may also contain one or more additional transgenes. Such transgene may be any nucleotide sequence encoding a protein or RNA molecule conferring a desirable trait including but not limited to increased insect resistance, increased water use efficiency, increased yield performance, increased drought resistance, increased seed quality, improved nutritional quality, and/or increased herbicide tolerance, in which the desirable trait is measured with respect to a rice plant lacking such additional transgene.

The methods of the present invention are therefore useful for, among other things, controlling weeds in a field while growing plants for the purpose of producing seed and/or plant parts comprising event 17314 for agricultural or research purposes, selecting for progeny comprising event 17314 for plant breeding or research purposes, and producing progeny plants and seeds comprising event 17314.

The plants, progeny, seeds, plant cells, plant parts (such as pollen, ovule, pod, flower, root or stem tissue, and leaves), and commodity products of the present invention may be evaluated for DNA composition, gene expression, and/or protein expression. Such evaluation may be done by using standard methods such as PCR, northern blotting, southern analysis, western blotting, immuno-precipitation, and ELISA or by using the methods of detection and/or the detection kits provided herein.

Methods of detecting the presence of materials specific to event 17314 in a sample are provided. One method consists of detecting the presence of DNA specific to and derived from a rice cell, tissue, or plant comprising event 17314. The method provides for a template DNA sample to be contacted with a primer pair that is capable of producing an amplicon from event 17314 DNA upon being subjected to conditions appropriate for thermal amplification, particularly an amplicon that contains at least 15 contiguous nucleotides of either SEQ ID NO: 1 or SEQ ID NO: 2 or the complements thereof. The amplicon is produced from a template DNA molecule derived from event 17314, so long as the template DNA molecule incorporates the specific and unique nucleotide sequences as set forth in SEQ ID NO: 1 and SEQ ID NO: 2. The amplicon may be single or double stranded DNA or RNA, depending on the polymerase selected for use in the production of the amplicon. The method provides for detecting the amplicon molecule produced in any such thermal amplification reaction, and confirming within the sequence of the amplicon the presence of the nucleotides corresponding to SEQ ID NO: 1 or SEQ ID NO: 2 or the complements thereof. The detection of the nucleotides corresponding to SEQ ID NO: 1 or SEQ ID NO: 2 or the complements thereof in the amplicon are determinative and/or diagnostic for the presence of event 17314 specific DNA and thus biological material comprising event 17314 in the sample.

Another method is provided for detecting the presence of a DNA molecule corresponding to SEQ ID NO: 3 and SEQ ID NO: 4 in a sample consisting of material derived from rice plant or rice plant tissue. The method consists of (i) extracting a DNA sample from a rice plant, or from a group of different rice plants, (ii) contacting the DNA sample with a DNA probe molecule that exhibits at least 15 contiguous nucleotides as set forth in either SEQ ID NO: 1 or SEQ ID NO: 2, (iii) allowing the probe and the DNA sample to hybridize under stringent hybridization conditions, and then (iv) detecting a hybridization event between the probe and the target DNA sample. Detection of the hybrid composition is diagnostic for the presence of SEQ ID NO: 3 or SEQ ID NO: 4, as the case may be, in the DNA sample. Absence of hybridization is alternatively diagnostic of the absence of the transgenic event in the sample. Alternatively, determining that a particular rice plant contains either or both of the sequences corresponding to SEQ ID NO: 1 or SEQ ID NO: 2, or the complements thereof, is determinative that the rice plant contains at least one allele corresponding to event 17314.

It is thus possible to detect the presence of a nucleic acid molecule of the present invention by any well known nucleic acid detection method such as the polymerase chain reaction (PCR) or DNA hybridization using nucleic acid probes. An event-specific PCR assay is discussed, for example, by Taverniers et al. (J. Agric. Food Chem., 53: 3041-3052, 2005) in which an event-specific tracing system for transgenic maize lines Bt11, Bt176, and GA21 and for canola event RT73 is demonstrated. In this study, event-specific primers and probes were designed based upon the sequences of the genome/ transgene junctions for each event. Transgenic plant event specific DNA detection methods have also been described in U.S. Pat. Nos. 6,893,826; 6,825,400; 6,740,488; 6,733,974; 6,689,880; 6,900,014 and 6,818,807.

DNA detection kits are provided. One type of kit contains at least one DNA molecule of sufficient length of contiguous nucleotides similar or complementary to SEQ ID NO: 3, SEQ ID NO: 5, or SEQ ID NO: 6 that functions as a DNA primer or probe specific for detecting the presence of DNA derived from transgenic rice event 17314 in a sample. The DNA molecule being detected with the kit contains at least 15 contiguous nucleotides as set forth in SEQ ID NO: 1, or the complement thereof. Alternatively, the kit may contain at least one DNA molecule of sufficient length of contiguous nucleotides similar or complementary to SEQ ID NO: 4, SEQ ID NO: 5, or SEQ ID NO: 6 to function as a DNA primer or probe specific for detecting the presence of DNA derived from transgenic rice event 17314 in a biological sample. The DNA molecule being detected with the kit contains at least 15 contiguous nucleotides as set forth in SEQ ID NO: 2, or the complement thereof.

An alternative kit employs a method in which the target DNA sample is contacted with a primer pair as described above, then performing a nucleic acid amplification reaction sufficient to produce an amplicon comprising at least 15 contiguous nucleotides of SEQ ID NO: 2 or the complement thereof. Detection of the amplicon and determining the presence of no fewer than 15 contiguous nucleotides of SEQ ID NO: 1 or SEQ ID NO: 2 or the complements thereof within the sequence of the amplicon is determinative of, or said another way, diagnostic for, the presence of event 17314 specific DNA in the target DNA sample.

A DNA molecule sufficient for use as a DNA probe is provided that is useful for determining, detecting, or for diagnosing the presence or even the absence of DNA specific and unique to event 17314 DNA in a sample. The DNA molecule contains at least 15 contiguous nucleotides of SEQ ID NO: 1, or the complement thereof, or at least 15 contiguous nucleotides of SEQ ID NO: 2, or the complement thereof.

Nucleic-acid amplification can be accomplished by any of the various nucleic-acid amplification methods known in the art, including thermal amplification methods. The sequence of the heterologous DNA insert, junction sequences, or flanking sequences from rice event 17314 (with representative seed samples comprising event 17314 deposited as ATCC PTA-9844) can be verified (and corrected if necessary) by amplifying such sequences from the event using primers derived from the sequences provided herein followed by standard DNA sequencing of the amplicon or of the cloned DNA.

The amplicon produced by these methods may be detected by a plurality of techniques. One such method is Genetic Bit Analysis (Nikiforov, et al. Nucleic Acid Res. 22:4167-4175, 1994) where a DNA oligonucleotide is designed which overlaps both the adjacent flanking genomic DNA sequence and the inserted DNA sequence. The oligonucleotide is immobilized in wells of a microwell plate. Following thermal amplification of the region of interest (using one primer in the inserted sequence and one in the adjacent flanking genomic sequence), a single-stranded amplicon (thermal amplification product) can be hybridized to the immobilized oligonucleotide and serve as a template for a single base extension reaction using a DNA polymerase and labelled ddNTPs specific for the expected next base. Readout may be fluorescent or ELISA-based. Detection of a fluorescent or other signal indicates the presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to a single-stranded thermal amplification product (single stranded amplicon) from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. ddNTPs are added individually and the incorporation results in a light signal which is measured. A light signal indicates the presence of the transgene insert/flanking sequence due to successful amplification, hybridization, and single or multi-base extension.

Fluorescence Polarization as described by Chen, et al., (Genome Res. 9:492-498, 1999) is a method that can be used to detect the amplicon. Using this method an oligonucleotide is designed which overlaps the genomic flanking and inserted DNA junction. The oligonucleotide is hybridized to single-stranded amplification product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TAQMAN® (PE Applied Biosystems, Foster City, Calif.) may also be used to detect and/or quantifying the presence of a DNA sequence using the instructions provided by the manufacturer. Briefly, a FRET oligonucleotide probe is designed which overlaps the genomic flanking and insert DNA junction. The FRET probe and amplification primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi, et al. (Nature Biotech. 14:303-308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and amplification primers (one primer in the insert DNA sequence and one in the flanking genomic sequence) are cycled in the presence of a thermostable polymerase and dNTPs. Following successful amplification, hybridization of the FRET probe to the target sequence results in the removal of the probe secondary structure and spatial separation of the fluorescent and quenching moieties, resulting in the production of a fluorescent signal. The fluorescent signal indicates the presence of the flanking/transgene insert sequence due to successful amplification and hybridization. Other methods known in the art may be used in practicing the methods of the invention, such as: microfluidics (see, for example, U.S. Patent pub. 2006068398 and U.S. Pat. No. 6,544,734), which provide methods and devices to separate and amplify DNA samples; optical dyes to detect and measure specific DNA molecules (see, for example, WO/05017181); nanotube devices (see, for example, WO/06024023) that comprise an electronic sensor for the detection of DNA molecules; and/or nanobeads that bind specific DNA molecules that may then be detected.

DNA detection kits can be developed using the compositions disclosed herein and the methods known in the art of DNA detection. The kits are useful for the identification of event 17314 in a sample and can be applied to methods for breeding rice plants containing the appropriate event DNA. The kits may contain DNA primers or probes that are similar or complementary to SEQ ID NO: 1-6, or fragments thereof. The kits and detection methods of the present invention are therefore useful for, among other things, identifying rice event 17314, selecting plant varieties or hybrids comprising event 17314, detecting the presence of DNA derived from rice event 17314 in a sample, and monitoring samples for the presence and/or absence of rice event 17314 or plants, plant parts or commodity products comprising event 17314.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Transformation of Rice and Event Selection

This example describes how transgenic rice events were created and how event 17314 was selected. The transgenic glyphosate tolerant event 17314 was generated by a particle gun-mediated transformation of rice cells with a transgene DNA fragment illustrated in FIG. 1, the sequence of which is set forth in SEQ ID NO: 5. The transgene DNA fragment comprises an expression cassette comprising a promoter (P-CaMV.e35S) molecule derived from Cauliflower Mosaic Virus comprising a duplicated enhancer, operably linked to an intron molecule (1-Os.Act1) derived from a rice actin 1 gene, operably linked to a DNA molecule encoding a chloroplast transit peptide (CTP2, *Arabidopsis thaliana* EPSPS), operably linked to a DNA molecule encoding a glyphosate resistant EPSPS (AGRtu.EPSPS:CP4), operably connected to a 3' transcription termination region DNA molecule (T-AGRtu.nos) derived from the *Agrobacterium tumefaciens* nopaline synthase gene.

Explants from rice variety M-202 were first transformed with one of four expression cassettes using a particle gun method. Transformed cells were then selected on media containing glyphosate and surviving cells were regenerated into plants. The transformation process generated 928 R0 plants, with each R0 plant being a separate, individual event. These 928 events were screened at the R0 stage by PCR and Southern analysis to eliminate multi-copy and/or molecularly complex events. For the PCR analysis, endpoint TAQMAN® assays were initially used with extracted DNA. Based on PCR screening, 565 R0 events were selected. These 565 R0 events were then screened by Southern analysis. For the Southern analysis, DNA was extracted from the rice tissue, digested with NcoI and EcoRI or SspI, and hybridized using Southern blot hybridization analysis techniques and radioactive DNA probes complementary to the CaMV 35S promoter and the EPSPS coding sequence. These data were used to determine the copy number of the transgene cassette inserted into the rice genome and to select 240 R0 events having single insertions.

These 240 selected events were then advanced to growth chambers for phenotypic and fertility analysis in order to identify off-type plants. From the growth chamber phenotypic and fertility screening, 170 events were selected for advancement. These 170 R1 events were then screened for glyphosate tolerance in growth chambers. These plants were also analyzed by secondary Southern analysis for intact transgene insertion. Using the data collected from these analyses, 19 events were selected for advancement. Subsequently, R2 plants for 13 of these events were advanced for field trials. Field trial data for multiple characteristics were collected for plants for each of the 13 events over one growing season and for 5 of the events over two growing seasons. In the first year field trials, the 13 events were tested for glyphosate tolerance and agronomic equivalence at a minimum of 3 locations in a multiple replication field trial design. The results are presented in Table 1.

TABLE 1

Field Trial Results from First Season Field Test Program

| Parameters | A | B | 17314 | C | D | E | F | G | H | I | J | K | L |
|---|---|---|---|---|---|---|---|---|---|---|---|---|---|
| Efficacy | | | | | | | | | | | | | |
| Vegetative Tolerance | Yes | Yes | Yes | Yes | Yes | Yes | Yes | Yes | Yes | Yes | Yes | Yes | Yes |
| Yield | Yes | Yes | Yes | Yes | No | Yes | Yes | Yes | Yes | Yes | No | Yes | Yes |
| Fertility, Phenotype, Maturity | No | Yes | Yes | Yes | Yes | Yes | No | Yes | Yes | Yes | Yes | Yes | Yes |
| Agronomic | | | | | | | | | | | | | |
| Yield | Yes | Yes | Yes | Yes | Yes | Yes | Yes | Yes | Yes | Yes | Yes | Yes | Yes |
| Fertility, Phenotype, Maturity | Yes | Yes | Yes | Yes | Yes | Yes | Yes | Yes | Yes | Yes | Yes | Yes | Yes |
| Field Test Pass? | No | Yes | Yes | Yes | No | Yes | No | Yes | Yes | Yes | No | Yes | Yes |

These data were then used to select five lead events which were advanced to second year field trials. In these second year field trials, the five lead events were tested for tolerance to glyphosate and agronomic equivalence in a 6 location multiple replication field trial design. The results are presented in Table 2.

TABLE 2

Field Trial Results from Second Season Field Test Program

| Parameters | Events | | | | |
|---|---|---|---|---|---|
| | B | 17314 | C | E | G |
| Efficacy | | | | | |
| Vegetative Tolerance | Yes | Yes | Yes | Yes | Yes |
| Yield | Yes | Yes | Yes | Yes | Yes |
| Fertility, Phenotype, Maturity | Yes | Yes | Yes | Yes | Yes |
| Agronomic | | | | | |
| Yield | Yes | Yes | Yes | Yes | Yes |
| Fertility, Phenotype, Maturity | Yes | Yes | Yes | Yes | Yes |
| Field Test Pass | Yes | Yes | Yes | Yes | Yes |

In the efficacy trial in the two seasons, the plants were treated at the 4-6 leaf stage of growth with a 3 pounds acid equivalent per acre (lb ae/ac) amount of glyphosate, which is twice a typical commercial rate, or a 4.5 lb ae/ac amount of glyphosate, which is three times a typical commercial rate. Vegetative glyphosate tolerance was measured as vegetative injury and reproductive glyphosate tolerance was measured as yield and percent (%) fertility. Using data from these trials, event 17314 was selected. Event 17314 showed no vegetative injury at either 3 lb ae/ac or 4.5 lb ae/ac and no yield loss after treatment with glyphosate, measured as tons/acre (T/ac) of rice grain.

Example 2

Isolation of Rice Chromosome Sequences Adjacent to Inserted DNA

Rice genomic DNA for all PCR reactions was isolated using a rapid high pH/high salt lysis protocol. For this protocol, approximately 0.1 g of lyophilized ground leaf tissue was mixed by vortexing with 600 ul (microliter) of lysis buffer (100 mM Tris, 1 M KCl, 10 mM EDTA, pH 9.5), followed by incubation at 65 degree Celcius for 45-60 minutes. Next, the tube was again vortexed and 200 ul of precipitation buffer was added (5 M potassium acetate, pH 7.0), vortexed again and centrifuged. A 600 ul aliquot of the DNA solution was transferred to a clean tube and 500 ul of ice cold isopropanol was added to precipitate the DNA. Following centrifugation, the DNA pellet was washed with 70% ethanol, air dried, and the DNA resuspended in 250 ul of water.

Extension of the rice genomic DNA adjacent to the transgene insertion was obtained for the 17314 event using the TAIL-PCR protocol essentially as described in Liu et al. (Plant Journal 8: 457-463, 1995). To identify the flanking genomic DNA, two sets of two nested genome-walking primers were designed near the flanking junctions. One set was designed to walk out of the 5' end of the integrated expression cassette and the other was designed to walk out of the 3' end of the integrated expression cassette.

The primers for the 5' TAIL-PCR are primer SQ1871 (SEQ ID NO: 12) for round 1 and primer SQ1869 (SEQ ID NO: 13) for round 2. The primers for the 3' TAIL-PCR are primer SQ1875 (SEQ ID NO: 10) for round 1 and primer SQ1880 (SEQ ID NO: 14) for round 2.

For identification of each flanking region, the two nested primers were used in successive PCR reactions with shorter arbitrary degenerate (AD) primers as described in Liu et al. (Plant Journal 8: 457-463, 1995). For the first round of PCR, for both 5' and 3' flanking sequence, the respective PCR reactions were set-up as detailed in Table 3. These reactions were carried out in an MJ Engine thermocycler with cycling parameters set forth in Table 4, with default ramp speed settings.

TABLE 3

Rice Event 17314 Round One TAIL-PCR Reactions

| Step | Reagent | Amount | Comments |
|---|---|---|---|
| 1 | 18 megohm water | add to final volume of 50 ul | — |
| 2 | 10X reaction buffer (with MgCl$_2$) | 5.0 ul | 1X final concentration of buffer, 1.5 mM final concentration of MgCl$_2$ |
| 3 | 10 mM solution of dATP, dCTP, dGTP, and dTTP | 1.0 ul | 200 µM final concentration of each dNTP |
| 4 | Primer SQ1871 (5' flank) or Primer SQ1875 (3' flank) (resuspended in 1X TE buffer or 18 megohm water to a concentration of 10 µM) | 1.0 ul | 0.2 µM final concentration |
| 5 | Arbitrary degenerate primer AD1, AD2 or AD3 (resuspended in 1X TE buffer or 18 megohm water to a concentration of 100 µM) | 1.5 ul | 3.0 µM final concentration Recommended to use all three arbitrary degenerate primers for maximum success rate |
| 6 | REDTaq DNA polymerase (1 unit/ul) | 2.5 ul | 2.5 unit/reaction (recommended to switch pipets prior to next step) |
| 7 | Extracted DNA (template): Targeted DNA Positive control DNA Nontransgenic DNA | 50-200 ng of genomic DNA | 1). Recommended to use high quality DNA as a template to increase success rate 2). Recommended to use positive control DNA from transgenic events from which the flanking sequence have been successfully isolated using this approach |

TABLE 4

Round One TAIL-PCR Thermocycling Conditions

| Cycle No. | Settings | |
|---|---|---|
| 1 | 94° C. | 2 minutes |
| 5 | 94° C. | 30 seconds |
|  | 62° C. | 1 minute |
|  | 72° C. | 2 minute and 30 seconds |
| 1 | 94° C. | 30 seconds |
|  | 25° C. | 3 minutes |
|  | ramping to 72° C. over 3 minutes (0.2° C./second) | |
|  | 72° C. | 2 minutes and 30 seconds |
| 15 | 94° C. | 10 seconds |
|  | 68° C. | 1 minute |
|  | 72° C. | 2 minutes and 30 seconds |
|  | 94° C. | 10 seconds |
|  | 68° C. | 1 minute |
|  | 72° C. | 2 minutes and 30 seconds |
|  | 94° C. | 10 seconds |
|  | 44° C. | 1 minute |
|  | 72° C. | 2 minutes and 30 seconds |
| 1 | 72° C. | 5 minutes |

An aliquot of the first round of TAIL-PCR was used for the second round of TAIL-PCR, as detailed in Table 5. These reactions were carried out in an MJ Engine thermocycler with cycling parameters set forth in Table 6, with default ramp speed setting.

TABLE 5

Round Two TAIL-PCR Reactions

| Step | Reagent | Amount | Comments |
|---|---|---|---|
| 1 | 18 megohm water | add to final volume of 50 ul | — |
| 2 | 10X reaction buffer (with MgCl$_2$) | 5.0 ul | 1X final concentration of buffer, 1.5 mM final concentration of MgCl$_2$ |
| 3 | 10 mM solution of dATP, dCTP, dGTP, and dTTP | 1.0 ul | 200 μM final concentration of each dNTP |
| 4 | Primer SQ1869 (5'flank) or Primer SQ1880 (3'flank) (resuspended in 1X TE buffer or 18 megohm water to a concentration of 10 μM) | 1.0 ul | 0.2 μM final concentration |
| 5 | Arbitrary degenerate primer (resuspended in 1X TE buffer or 18 megohm water to a concentration of 100 μM) | 1.0 ul | 2.0 μM final concentration |
| 6 | REDTaq DNA polymerase (1 unit/ul) | 2.5 ul | 2.5 unit/reaction (recommended to switch pipets prior to next step) |
| 7 | 1:100 dilution of Round One TAIL-PCR reaction | 5.0 ul | |

TABLE 6

Round Two TAIL-PCR Thermocycling Conditions

| Cycle No. | Settings | |
|---|---|---|
| 1 | 94° C. | 2 minutes |
| 12 | 94° C. | 10 seconds |
|  | 64° C. | 1 minute |
|  | 72° C. | 2 minutes and 30 seconds |
|  | 94° C. | 10 seconds |
|  | 64° C. | 1 minutes |
|  | 72° C. | 2 minutes and 30 seconds |
|  | 94° C. | 10 seconds |
|  | 44° C. | 1 minute |
|  | 72° C. | 2 minutes and 30 seconds |
| 10 | 94° C. | 15 seconds |
|  | 44° C. | 1 minute |
|  | 72° C. | 2 minutes and 30 seconds |
| 1 | 72° C. | 5 minutes |

To visualize the TAIL-PCR amplicons, aliquots of the round two reaction were run on 2.0% agarose gels and stained with ethidium bromide. Additionally, aliquots of the second round of TAIL-PCR were submitted to Monsanto genomic sequencing center to be sequenced. Sequence analysis was conducted with Monsanto proprietary Flanking Sequence Application sequence analysis software. PCR primers were designed to confirm the genomic flanking sequences observed in the sequencing results of the second-round TAIL-PCR reactions. For event 17314, the 5' genomic flanking sequence was confirmed by PCR reactions with primer pair SQ3629 (SEQ ID NO: 15) and SQ1869 (SEQ ID NO: 13). For event 17314, the 3' genomic flanking sequence was confirmed by PCR reactions with primer pair SQ3627 (SEQ ID NO: 16) and SQ1875 (SEQ ID NO: 10).

Example 3

Event Specific Endpoint TAQMAN® Assays

This example describes an event specific endpoint TAQMAN® thermal amplification method developed to identify event 17314 in a sample. Examples of conditions useful with this method are described in Table 7 and Table 8. DNA molecules useful in the method are, for example, primers SQ4183 (SEQ ID NO: 7) and SQ4191 (SEQ ID NO: 8) and the 6FAM™-labeled oligonucleotide probe PB1491 (SEQ ID NO: 9). Other probes and primers may be designed based upon the sequences of the transgene insert and/or the flanking sequences provided herein. SQ4183 (SEQ ID NO: 7) and SQ4191 (SEQ ID NO: 8) when used in these reaction methods with PB 1491 (SEQ ID NO: 9) produce a DNA amplicon that is diagnostic for event 17314 DNA. The controls for this analysis include a positive control from rice containing event 17314 DNA, a negative control from non-transgenic rice, and a negative control that contains no template DNA.

These assays are optimized for use with an Applied Biosystems GeneAmp PCR System 9700 or Stratagene Robocycler, MJ Engine, Perkin-Elmer 9700, or Eppendorf Mastercycler Gradient thermocycler. Other methods and apparatus are known to those skilled in the art that would be useful to produce amplicons for identifying the event 17314 DNA in a biological sample. The cycling parameters set forth in Table 7 and Table 8 may be used when analyzing samples. When conducting thermal amplifications in the Eppendorf Mastercycler Gradient or MJ Engine, the thermocycler should be run in the calculated mode. When conducting thermal amplifications in the Perkin-Elmer 9700, the thermocycler should be set with the ramp speed at maximum.

TABLE 7

Rice Event 17314 Specific Endpoint TAQMAN ®

| Step | Reagent | Volume | Comments |
|---|---|---|---|
| 1 | 18 megohm water | adjust for final volume of 10 µl | |
| 2 | 2X Universal Master Mix (dNTPs, enzyme, buffer) | 5.0 µl | 1X final concentration |
| 3 | Primer-1 and Primer-2 Mix (resuspended in 18 megohm water to a concentration of 20 uM for each primer) Example: In a microcentrifuge tube, the following should be added to achieve 500 µl at a final concentration of 20 uM: 100 µl of Primer SQ4183 (SEQ ID NO: 7) at a concentration of 100 µM; 100 µl of Primer SQ4191 (SEQ ID NO: 8) at a concentration of 100 µM; 300 µl of 18 megohm water | 0.5 µl | 1.0 µM final concentration |
| 4 | Event 6-FAM ™ MGB Probe PB1491 (SEQ ID NO: 9) (resuspended in 18 megohm water to a concentration of 10 µM) | 0.2 µl | 0.2 µM final concentration |
| 5 | Extracted DNA (template): 1. Leaf Samples to be analyzed 2. Negative control (non-transgenic DNA) 3. Negative water control (no template) 4. Positive control 17314 DNA | 3.0 µl | |

TABLE 8

Endpoint TAQMAN ® Thermocycler Conditions

| Cycle No. | Settings | |
|---|---|---|
| 1 | 50° C. | 2 minutes |
| 1 | 95° C. | 10 minutes |
| 10 | 95° C. | 15 seconds |
| | 64° C. | 1 minute |
| | −1° C./cycle | |
| 30 | 95° C. | 15 seconds |
| | 54° C. | 1 minute |
| 1 | 10° C. | Forever |

Example 4

Identification of Event 17314 in Breeding Activity

This example describes how one may identify event 17314 within the progeny of any breeding activity using rice comprising event 17314. DNA event primer pairs are used to produce an amplicon diagnostic for event 17314. An amplicon diagnostic for event 17314 comprises at least one junction sequence, provided herein as SEQ ID NO: 1 or SEQ ID NO: 2 ([A] and [B], respectively as illustrated in FIG. 1). SEQ ID NO: 1 ([A] of FIG. 1) is a nucleotide sequence corresponding to the junction of the flanking sequence with the 5' end of transgene insert (283 through 302 of SEQ ID NO: 3 [C], see FIG. 1). SEQ ID NO: 2 ([B], see FIG. 1) is a nucleotide sequence corresponding to the junction of the flanking sequence with the 3' end of transgene insert (positions 666 through 685 of SEQ ID NO: 4 [D], see FIG. 1).

Event primer pairs that will produce a diagnostic amplicon for event 17314 include primer pairs designed using the flanking sequences (SEQ ID NO: 3 and 4) and the inserted transgenic DNA sequence (SEQ ID NO: 5). To acquire a diagnostic amplicon in which at least 11 nucleotides of SEQ ID NO: 1 is found, one would design a forward primer molecule based upon SEQ ID NO: 3 from bases 1 through 292 and a reverse primer molecule based upon the inserted expression cassette DNA sequence, SEQ ID NO: 5 from positions 1 through 3,114 in which the primer molecules are of sufficient length of contiguous nucleotides to specifically hybridize to SEQ ID NO: 3 and SEQ ID NO: 5. To acquire a diagnostic amplicon in which at least 11 nucleotides of SEQ ID NO: 2 is found, one would design a forward primer molecule based upon the inserted expression cassette, SEQ ID NO: 5 from positions 1 through 3,114 and a reverse primer molecule based upon the 3' flanking sequence, SEQ ID NO: 4 from bases 1 through 675, in which the primer molecules are of sufficient length of contiguous nucleotides to specifically hybridize to SEQ ID NO: 4 and SEQ ID NO: 5. For practical purposes, one should design primers which produce amplicons of a limited size range, for example, between 100 to 1000 bases. Smaller (shorter polynucleotide length) sized amplicons in general may be more reliably produced in PCR reactions, allow for shorter cycle times, and be easily separated and visualized on agarose gels or adapted for use in endpoint TAQMAN®-like assays. Smaller amplicons can be produced and detected by methods known in the art of DNA amplicon detection. In addition, amplicons produced using primer pairs can be cloned into vectors, propagated, isolated and sequenced or can be sequenced directly with methods well established in the art. Any primer pair derived from the combination of SEQ ID NO: 3 and SEQ ID NO: 5 or the combination of SEQ ID NO: 4 and SEQ ID NO: 5 that are useful in a DNA amplification method to produce an amplicon diagnostic for event 17314 or progeny thereof is an aspect of the present invention. Any single isolated DNA polynucleotide primer molecule comprising at least 11 contiguous nucleotides of SEQ ID NO: 3, or its complement, that is useful in a DNA amplification method to produce an amplicon diagnostic for plants comprising event 17314 or progeny thereof is an aspect of the present invention. Any single isolated DNA polynucleotide primer molecule comprising at least 11 contiguous nucleotides of SEQ ID NO: 4, or its complement that is useful in a DNA amplification method to produce an amplicon diagnostic for plants comprising event 17314 or progeny thereof is an aspect of the present invention. Any single isolated DNA polynucleotide primer molecule comprising at least 11 contiguous nucleotides of SEQ ID NO: 5, or its complement that is useful in a DNA amplification method to produce an amplicon diagnostic for plants comprising event 17314 or progeny thereof is an aspect of the present invention.

An example of the amplification conditions for this analysis is illustrated in Table 7 and Table 8. However, any modification of these methods or the use of DNA primers homologous or complementary to SEQ ID NO: 3 or SEQ ID NO: 4 or DNA sequences of the transgene insert (SEQ ID NO: 5) of event 17314 that produce an amplicon diagnostic for event 17314 is within the scope of the present disclosure. A diagnostic amplicon comprises a DNA molecule homologous or complementary to at least one transgene/genomic junction DNA (SEQ ID NO: 1 or SEQ ID NO: 2), or a substantial portion thereof.

An analysis for event 17314 in a sample may include a positive control from event 17314, a negative control from a rice plant that is not event 17314 (for example, but not limited to, M-202), and/or a negative control that contains no rice genomic DNA. A primer pair that will amplify an endogenous rice DNA molecule may serve as an internal control for the DNA amplification conditions. Any fragment of a sequence selected from sequences as set forth in SEQ ID NO: 3, SEQ ID NO: 4, or SEQ ID NO: 5 may be used as a DNA amplification primer for the production of an amplicon by the methods shown in Table 7 and Table 8 and such an amplicon may be diagnostic for event 17314 when using event 17314 as template for such diagnostic amplification reaction. The use of these DNA primer sequences with modifications to the methods of Table 7 and Table 8 are within the scope of the invention. The amplicon produced by at least one DNA primer sequence derived from SEQ ID NO: 3, SEQ ID NO: 4, or SEQ ID NO: 5 that is diagnostic for event 17314 is an aspect of the invention.

DNA detection kits, which contain at least one DNA primer of sufficient length of contiguous nucleotides derived from SEQ ID NO: 3, SEQ ID NO: 4, or SEQ ID NO: 5 and that when used in a DNA amplification method produces a diagnostic amplicon for a plant comprising event 17314 or its progeny, may thus be designed and are an aspect of the invention. A rice plant part or seed or commodity product that will produce an amplicon diagnostic for event 17314 when tested in a DNA amplification method is an aspect of the invention. The assay for the event 17314 amplicon can be performed by using an Applied Biosystems GeneAmp® PCR System 9700 or Stratagene RoboCycler®, or MJ Engine, or Perkin-Elmer 9700, or Eppendorf Mastercycler® Gradient thermocycler or any other amplification system that can be used to produce an amplicon diagnostic of event 17314 as shown in Table 8.

A deposit of a representative sample of seed comprising rice event 17314 disclosed above and recited in the claims has been made under the Budapest Treaty with the American Type Culture Collection (ATCC), 10801 University Boulevard, Manassas, Va. 20110. The date of the deposit was Feb. 18, 2009. The ATCC accession number for this deposit is PTA-9844. The deposit will be maintained in the depository for a period of 30 years, or 5 years after the last request, or for the effective life of the patent, whichever is longer, and will be replaced as necessary during that period.

Having illustrated and described the principles of the present invention, it should be apparent to persons skilled in the art that the invention can be modified in arrangement and detail without departing from such principles. We claim all modifications that are within the spirit and scope of the appended claims.

We claim:

1. A recombinant DNA molecule comprising:
a sequence selected from the group consisting of SEQ ID NO: 1, SEQ ID NO: 2, SEQ ID NO: 3, SEQ ID NO: 4 and SEQ ID NO:6, and complete complements thereof.

2. The DNA molecule of claim 1, comprising the nucleotide sequence of SEQ ID NO:6.

3. The DNA molecule of claim 1, wherein said DNA molecule is from event 17314, a representative sample of seed comprising event 17314 having been deposited under ATCC Accession No. PTA-9844.

4. The DNA molecule of claim 1, wherein said DNA molecule is comprised in a rice plant, plant cell, seed, progeny plant, plant part, or commodity product.

5. The DNA molecule of claim 1, wherein said DNA molecule is an amplicon produced from a template molecule from event 17314.

6. A polynucleotide probe diagnostic for the presence of event 17314, wherein said probe is at least 18 nucleotides in length and is of sufficient length to bind to a sequence of at least 11 contiguous nucleotides of a sequence selected from the group consisting of SEQ ID NO: 1 and SEQ ID NO: 2, and complete complements thereof.

7. A pair of DNA molecules consisting of a first DNA molecule and a second DNA molecule different from the first DNA molecule, wherein said DNA molecules have a nucleotide sequence of sufficient length of contiguous nucleotides of SEQ ID NO: 6, or a complete complement thereof, and wherein said first DNA molecule resides in a transgene insert DNA sequence of SEQ ID NO: 6, and said second DNA molecule resides in the rice genomic DNA sequence of SEQ ID NO: 6, to function as DNA primers when used together in an amplification reaction with a template from rice event 17314 to produce an amplicon diagnostic for rice event 17314 in a sample, and wherein said amplicon comprises the nucleotide sequences of SEQ ID NO: 1 or SEQ ID NO: 2.

8. The pair of DNA molecules of claim 7, wherein said amplicon comprises a nucleotide sequence selected from the group consisting of SEQ ID NO: 1 and SEQ ID NO: 2, and complements thereof.

9. A method of detecting the presence of a DNA molecule from rice event 17314 comprising:
   (a) contacting a DNA sample with a pair of DNA molecules of claim 7;
   (b) performing an amplification reaction sufficient to produce an amplicon comprising a polynucleotide molecule having at least 11 contiguous nucleotides of a sequence selected from the group consisting of SEQ ID NO: 1 and SEQ ID NO: 2, and complete complements thereof; and
   (c) detecting said DNA amplicon, wherein detection of said DNA amplicon is diagnostic for the presence of said DNA molecule from rice event 17314 in said DNA sample.

10. A method of detecting the presence of a DNA molecule comprising a nucleotide sequence selected from the group consisting of SEQ ID NO: 3 or SEQ ID NO: 4 in a sample comprising:
    (a) contacting a sample with a DNA probe comprising a polynucleotide sequence selected from the group consisting of SEQ ID NO: 1 and SEQ ID NO: 2, and complete complements thereof, wherein said DNA probe hybridizes under stringent hybridization conditions with a DNA molecule comprising a nucleotide sequence selected from the group consisting of SEQ ID NO: 3 or SEQ ID NO: 4 and does not hybridize under the stringent hybridization conditions with a DNA molecule not comprising a nucleotide sequence selected from the group consisting of SEQ ID NO: 3 or SEQ ID NO: 4;
    (b) subjecting said sample and said DNA probe to stringent hybridization conditions; and
    (c) detecting hybridization of said DNA probe to said DNA molecule comprising a nucleotide sequence selected from the group consisting of SEQ ID NO: 3 or SEQ ID NO: 4.

11. A DNA detection kit comprising the pair of DNA molecules of claim 7.

12. A DNA detection kit comprising at least one DNA probe diagnostic for rice event 17314, wherein the DNA probe comprises at least 24 contiguous nucleotides of SEQ ID NO:1 or SEQ ID NO:2 or a complete complement thereof.

13. A method of detecting the presence of a DNA molecule from rice event 17314, said method comprising:
    (a) contacting a sample with the pair of DNA molecules of claim 7;
    (b) performing a nucleic acid amplification reaction sufficient to produce an amplicon comprising at least 15 contiguous nucleotides of SEQ ID NO:1 or SEQ ID NO:2, or a complete complement thereof; and
    (c) detecting said amplicon.

14. A rice plant, seed, cell, or plant part thereof comprising a polynucleotide molecule comprising a nucleotide sequence selected from the group consisting of SEQ ID NO: 1, SEQ ID NO: 2, and complete complements thereof.

15. The rice plant, seed, cell, or plant part thereof of claim 14, wherein said plant, seed, cell, or plant part thereof is tolerant to glyphosate herbicide treatment.

16. The rice plant, seed, cell, or plant part thereof of claim 14, the genome of which produces an amplicon diagnostic for event 17314 when tested in a DNA amplification method.

17. A rice plant, seed, cell, or plant part thereof comprising event 17314, wherein a representative sample of seed comprising event 17314 having been deposited under ATCC Accession No. PTA-9844.

18. The rice plant, seed, cell, or plant part thereof of claim 17, wherein the plant or part thereof is tolerant to glyphosate herbicide treatment.

19. The rice plant, seed, cell, or plant part thereof of claim 17, wherein said rice plant or seed is a hybrid having at least one parent comprising event 17314, a representative sample of seed comprising event 17314 having been deposited under ATCC Accession No. PTA-9844.

20. The rice plant, seed, cell, or plant part thereof of claim 17, defined as a cell, pollen, ovule, pod, flower, root tissue, stem tissue, or leaf tissue.

21. The rice plant, seed, cell, or plant part thereof of claim 17, further defined as a progeny plant of any generation of a rice plant comprising said event 17314.

22. A rice commodity product comprising a DNA molecule selected from the group consisting of SEQ ID NO: 1 and SEQ ID NO: 2.

23. The rice commodity product of claim 22, further defined as a commodity product selected from the group consisting of whole or processed rice seeds, animal feed, oil, meal, flour, flakes, bran, puffed rice, milk, cheese, paper, cream, wine, alcohol, biomass, and fuel products.

24. The rice commodity product of claim 22, wherein the commodity product comprises event 17314, representative seed comprising said event 17314 having been deposited under ATCC Accession No. PTA-9844.

25. The rice commodity product of claim 22, further defined as comprising a nucleic acid that produces an amplicon diagnostic for event 17314 when tested in a DNA amplification method.

26. A rice plant or part thereof capable of producing an event 17314 diagnostic amplicon when tested in a DNA amplification method, representative seed comprising said event 17314 having been deposited under ATCC Accession No. PTA-9844.

27. The rice plant of claim 26, wherein the amplicon comprises SEQ ID NO:1 or SEQ ID NO:2.

28. A rice seed capable of producing an event 17314 diagnostic amplicon when tested in a DNA amplification method, representative seed comprising said event 17314 having been deposited under ATCC Accession No. PTA-9844.

29. The rice seed of claim 28, wherein the amplicon comprises SEQ ID NO:1 or SEQ ID NO:2.

30. A method of producing a rice plant tolerant to glyphosate herbicide comprising introducing into the genome of said plant event 17314, representative seed comprising said event 17314 having been deposited under ATCC Accession No. PTA-9844.

31. The method of claim 30, defined as comprising the steps of: (a) crossing a first rice plant comprising event 17314 with a second rice plant lacking event 17314 to produce progeny plants; and (b) selecting at least a first progeny plant that comprises said event 17314 and is tolerant to glyphosate.

32. The method of claim 31, further comprising selfing said first progeny plant to produce second generation progeny plants and selecting at least a first plant homozygous for said event 17314.

33. A method of producing a rice commodity product comprising, (a) obtaining the rice plant or part thereof of claim 17; and (b) producing a rice commodity product from the rice plant or part thereof.

34. The method of claim 33, wherein the commodity product is selected from the group consisting of whole or processed rice seeds, animal feed, oil, meal, flour, flakes, bran, puffed rice, milk, cheese, paper, cream, wine, alcohol, biomass, and fuel products.

35. A method for controlling the growth of weeds in a field comprising rice plants comprising event 17314, the method comprising treating the field with an amount of glyphosate effective to control the growth of weeds, wherein the rice plants exhibit tolerance to the glyphosate.

36. The method of claim 35, wherein said effective amount of glyphosate is from about 0.5 pounds to about 4.5 pounds per acre.

37. A nonliving plant material comprising a DNA molecule selected from the group consisting of SEQ ID NO: 1, SEQ ID NO: 2 and complete complements thereof.

38. A microorganism comprising a polynucleotide molecule having a nucleotide sequence selected from the group consisting of the complete length of SEQ ID NO: 1, the complete length of SEQ ID NO: 2, and complete complements thereof.

39. The microorganism of claim 38, wherein said microorganism is a plant cell.

* * * * *

UNITED STATES PATENT AND TRADEMARK OFFICE
CERTIFICATE OF CORRECTION

PATENT NO.       : 8,618,360 B2                          Page 1 of 1
APPLICATION NO.  : 13/146634
DATED            : December 31, 2013
INVENTOR(S)      : Yun-Chia Sophia Chen et al.

It is certified that error appears in the above-identified patent and that said Letters Patent is hereby corrected as shown below:

In the Claims

Column 40, Line 59, please delete "molecules have a", and insert --molecules comprising a--

Signed and Sealed this
Eleventh Day of March, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,618,360 B2 | Page 1 of 1 |
| APPLICATION NO. | : 13/146634 | |
| DATED | : December 31, 2013 | |
| INVENTOR(S) | : Chen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 142 days.

Signed and Sealed this
Thirteenth Day of October, 2015

Michelle K. Lee
*Director of the United States Patent and Trademark Office*

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: chimeric DNA of transgene insert DNA and rice
      DNA

<400> SEQUENCE: 1
tattggtaaa gccgcgttaa                                              20

<210> SEQ ID NO 2
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Chimeric DNA of transgene insert DNA and rice
      DNA

<400> SEQUENCE: 2
cgtaggcgtc cttggtaccg                                              20

<210> SEQ ID NO 3
```

```
<211> LENGTH: 302
<212> TYPE: DNA
<213> ORGANISM: Artificial sequence
<220> FEATURE:
<221> NAME/KEY: misc_feature
<222> LOCATION: (1)..(302)
<223> OTHER INFORMATION: Chimeric DNA of transgene insert DNA and rice
      DNA

<400> SEQUENCE: 3
aggaacgtct tgagattcag gcaattgcag atgatagctc aattctaaca taattaccct      60
aatatagctg gctctttggg gtatttgaat attctccaag aattctggtg catttaccgt     120
tattgcttct gtaaacatag tagctaaata atcccaacgt gttacataag gtaagtattg     180
tataatagtt cgggatctgc ggataagaat atttgtccat ctgtaatgga gattacatta     240
gtaggaatat aggcggaaac gtctccagta ttgagtctca actattggta aagccgcgtt     300
aa                                                                    302

<210> SEQ ID NO 4
<211> LENGTH: 685
<212> TYPE: DNA
<213> ORGANISM: Artificial sequence
<220> FEATURE:
<221> NAME/KEY: misc_feature
<222> LOCATION: (1)..(685)
<223> OTHER INFORMATION: Chimeric DNA of transgene insert DNA and rice
      DNA

<400> SEQUENCE: 4
tttttccttt tattttagga attttgggaa catttcaaca aaggaggtct ttcacaggtc      60
gagcggacgg gaaaaccttc tttggatttg cccaagatct ttggaattca tttatttctt     120 gcagggggtgg cttgctttgg ctttggcgca tttgaaatga aattaaatct ttatgtactg    180
actcctaagc gaattatttg ggattgtgaa gtgaaagaaa tcattttatc tactaatagt     240
ggccaaattg gcgtattacc aaaccacgcc cccattaaca cagctgtaga tatgaggagc     300
atcttgtgtt cgatctttcc aaagatcaaa aagaataaga acttcctatt taatatatag     360
agcatagata gaatacaaaa tacaaatcaa cttgtctgat ttccattaga tattatttca     420
tatgtatcga gggtattcat ctaatatatg gaccaaagag agactatttt ttctggatcc     480
aaaattaata aaataaacaa atcaattttt ttcaatttta aaataaggaa taaatcatgt     540
atacatctaa acaacccttt cataaatcca aacaaacttt tcataaatcc aagcaaactt     600
ttcgtaaatc caagcaaact tttcgtaaat tcaaacaacc ttttcgcaaa cccaaacaac     660 ctttttcgtag gcgtccttgg taccg                                          685

<210> SEQ ID NO 5
<211> LENGTH: 3114
<212> TYPE: DNA
<213> ORGANISM: Artificial sequence
<220> FEATURE:
<221> NAME/KEY: misc_feature
<222> LOCATION: (1)..(3114)
<223> OTHER INFORMATION: Chimeric transgene DNA

<400> SEQUENCE: 5
gccgcgttaa caagcttctg caggtccgat tgagactttt caacaaaggg taatatccgg      60
aaacctcctc ggattccatt gcccagctat ctgtcacttt attgtgaaga tagtggaaaa     120
ggaaggtggc tcctacaaat gccatcattg cgataaagga aaggccatcg ttgaagatgc     180
ctctgccgac agtggtccca agatggaccc ccacccacg aggagcatcg tggaaaaaga     240
```

```
agacgttcca accacgtctt caaagcaagt ggattgatgt gatggtccga ttgagacttt      300
tcaacaaagg gtaatatccg gaaacctcct cggattccat tgcccagcta tctgtcactt      360
tattgtgaag atagtggaaa aggaaggtgg ctcctacaaa tgccatcatt gcgataaagg      420
aaaggccatc gttgaagatg cctctgccga cagtggtccc aaagatggac ccccacccac      480
gaggagcatc gtggaaaaag aagacgttcc aaccacgtct tcaaagcaag tggattgatg      540
tgatatctcc actgacgtaa gggatgacgc acaatcccac tatccttcgc aagacccttc      600
ctctatataa ggaagttcat ttcatttgga gaggacacgc tgacaagctg actctagcag      660
atcctctaga accatcttcc acacactcaa gccacactat ggagaacaca cagggacaa       720 cacaccataa gatccaaggg aggcctccgc cgccgccggt aaccaccccg cccctctcct      780 cttctttct ccgtttttt ttccgtctcg gtctcgatct ttggccttgg tagtttgggt       840
gggcgagagg cggcttcgtg cgcgcccaga tcggtgcgcg ggaggggcgg gatctcgcgg      900
ctggggctct cgccggcgtg gatccggccc ggatctcgcg gggaatgggg ctctcggatg      960
tagatctgcg atccgccgtt gttggggggag atgatggggg gtttaaaatt tccgccgtgc    1020
taaacaagat caggaagagg ggaaaagggc actatggttt atatttttat atatttctgc    1080
tgcttcgtca ggcttagatg tgctagatct ttctttcttc tttttgtggg tagaatttga    1140
atccctcagc attgttcatc ggtagttttt cttttcatga tttgtgacaa atgcagcctc    1200
gtgcggagct tttttgtagg tagaagtgat caaccatggc gcaagttagc agaatctgca    1260
atggtgtgca gaacccatct cttatctcca atctctcgaa atccagtcaa cgcaaatctc    1320
ccttatcggt ttctctgaag acgcagcagc atccacgagc ttatccgatt tcgtcgtcgt    1380
ggggattgaa gaagagtggg atgacgttaa ttggctctga gcttcgtcct cttaaggtca    1440
tgtcttctgt ttccacggcg tgcatgctac acggtgcaag cagccggccg gcaaccgctc    1500
gcaaatcttc cggcctttcg ggaacggtca ggattccggg cgataagtcc atatcccacc    1560
ggtcgttcat gttcggcggt cttgccagcg gtgagacgcg catcacgggc ctgcttgaag    1620
gtgaggacgt gatcaatacc gggaaggcca tgcaggctat gggagcgcgt atccgcaagg    1680
aaggtgacac atggatcatt gacggcgttg ggaatggcgc tctgctcgcc cctgaggccc    1740
ctctcgactt cggcaatgcg gcgacgggct gcaggctcac tatgggactg gtcggggtgt    1800
acgacttcga tagcacgttc atcggagacg cctcgctcac aaagcgccca atgggccgcg    1860
ttctgaaccc gttgcgcgag atgggcgtac aggtcaaatc cgaggatggt gaccgtttgc    1920
ccgttacgct gcgcgggccg aagacgccta ccccgattac ctaccgcgtg ccaatggcat    1980
ccgcccaggt caagtcagcc gtgctcctcg ccggactgaa cactccgggc atcaccacgg    2040
tgatcgagcc catcatgacc agggatcata ccgaaaagat gcttcagggg tttggcgcca    2100
acctgacggt cgagacggac gctgacggcg tcaggaccat ccgccttgag ggcaggggta    2160
aactgactgg ccaagtcatc gatgttccgg gagacccgtc gtccacggcc ttcccgttgg    2220
ttgcggcgct gctcgtgccg gggagtgacg tgaccatcct gaacgtcctc atgaacccga    2280
ccaggaccgg cctgatcctc acgcttcagg agatgggagc cgacatcgag gtgatcaacc    2340
cgcgcctggc aggcggtgaa gacgttgcgg atctgcgcgt gcgctcctct accctgaagg    2400
gcgtgacggt cccggaagat cgcgcgccgt ccatgataga cgagtatcct attctggccg    2460
tcgccgctgc gttcgccgaa ggggccacgg tcatgaacgg tcttgaggaa ctccgcgtga    2520
aggaatcgga tcgcctgtcg gcggtggcca atggcctgaa gctcaacggt gttgactgcg    2580
acgagggtga gacctcactc gtggtccgtg gccggcctga tggcaagggc ctcggcaacg    2640
```

-continued

| | |
|---|---|
| ccagtggagc ggccgtcgcc acgcacctcg atcatcgcat cgcgatgtcc ttcttggtga | 2700 |
| tgggtctcgt ctcagagaac ccggtgaccg tcgatgacgc cacgatgata gcgacgagct | 2760 |
| tcccagagtt catggatctg atggcgggcc tcggggccaa gatcgaactg tctgacacga | 2820 |
| aggccgcttg aattcccgat cgttcaaaca tttggcaata aagtttctta agattgaatc | 2880 |
| ctgttgccgg tcttgcgatg attatcatat aatttctgtt gaattacgtt aagcatgtaa | 2940 |
| taattaacat gtaatgcatg acgttattta tgagatgggt ttttatgatt agagtcccgc | 3000 |
| aattatacat ttaatacgcg atagaaaaca aaatatagcg cgcaaactag gataaattat | 3060 |
| cgcgcgcggt gtcatctatg ttactagatc ggggatgggg aattcggtac caag | 3114 |

<210> SEQ ID NO 6
<211> LENGTH: 4081
<212> TYPE: DNA
<213> ORGANISM: Artificial sequence
<220> FEATURE:
<221> NAME/KEY: misc_feature
<222> LOCATION: (1)..(4081)
<223> OTHER INFORMATION: Chimeric DNA of transgene insert DNA and Rice
      DNA

<400> SEQUENCE: 6

| | |
|---|---|
| aggaacgtct tgagattcag gcaattgcag atgatagctc aattctaaca taattaccct | 60 |
| aatatagctg gctctttggg gtatttgaat attctccaag aattctggtg catttaccgt | 120 |
| tattgcttct gtaaacatag tagctaaata atcccaacgt gttacataag gtaagtattg | 180 |
| tataatagtt cgggatctgc ggataagaat atttgtccat ctgtaatgga gattacatta | 240 |
| gtaggaatat aggcggaaac gtctccagta ttgagtctca actattggta aagccgcgtt | 300 |
| aacaagcttc tgcaggtccg attgagactt ttcaacaaag ggtaatatcc ggaaacctcc | 360 |
| tcggattcca ttgcccagct atctgtcact ttattgtgaa gatagtggaa aggaaggtg | 420 |
| gctcctacaa atgccatcat tgcgataaag gaaaggccat cgttgaagat gcctctgccg | 480 |
| acagtggtcc caaagatgga ccccacccca cgaggagcat cgtggaaaaa gaagacgttc | 540 |
| caaccacgtc ttcaaagcaa gtggattgat gtgatggtcc gattgagact ttcaacaaa | 600 |
| gggtaatatc cggaaacctc ctcggattcc attgcccagc tatctgtcac tttattgtga | 660 |
| agatagtgga aaggaaggt ggctcctaca aatgccatca ttgcgataaa ggaaaggcca | 720 |
| tcgttgaaga tgcctctgcc gacagtggtc ccaaagatgg accccacccc acgaggagca | 780 |
| tcgtggaaaa agaagacgtt ccaaccacgt cttcaaagca agtggattga tgtgatatct | 840 |
| ccactgacgt aagggatgac gcacaatccc actatccttc gcaagaccct tcctctatat | 900 |
| aaggaagttc atttcatttg gagaggacac gctgacaagc tgactctagc agatcctcta | 960 |
| gaaccatctt ccacacactc aagccacact attggagaac acagggac aacacaccat | 1020 |
| aagatccaag ggaggcctcc gccgccgccg taaccacccc gcccctctc ctctttcttt | 1080 |
| ctccgttttt ttttccgtct cggtctcgat cttttggcctt ggtagtttgg gtgggcgaga | 1140 |
| ggcggcttcg tgcgcgccca gatcggtgcg cggaggggc gggatctcgc ggctggggct | 1200 |
| ctcgccggcg tggatccggc ccggatctcg cggggaatgg ggctctcgga tgtagatctg | 1260 |
| cgatccgccg ttgttggggg agatgatggg gggtttaaaa tttccgccgt gctaaacaag | 1320 |
| atcaggaaga ggggaaaagg gcactatggt ttatattttt atatatttct gctgcttcgt | 1380 |
| caggcttaga tgtgctagat ctttcttttct tcttttttgtg ggtagaattt gaatccctca | 1440 |
| gcattgttca tcggtagttt ttcttttcat gatttgtgac aaatgcagcc tcgtgcggag | 1500 |
| cttttttgta ggtagaagtg atcaaccatg gcgcaagtta gcagaatctg caatggtgtg | 1560 |

```
cagaacccat ctcttatctc caatctctcg aaatccagtc aacgcaaatc tcccttatcg    1620
gtttctctga agacgcagca gcatccacga gcttatccga tttcgtcgtc gtggggattg    1680
aagaagagtg ggatgacgtt aattggctct gagcttcgtc ctcttaaggt catgtcttct    1740
gtttccacgg cgtgcatgct acacggtgca agcagccggc cggcaaccgc tcgcaaatct    1800
tccggccttt cgggaacggt caggattccg ggcgataagt ccatatccca ccggtcgttc    1860
atgttcggcg gtcttgccag cggtgagacg cgcatcacgg gcctgcttga aggtgaggac    1920
gtgatcaata ccgggaaggc catgcaggct atgggagcgc gtatccgcaa ggaaggtgac    1980
acatggatca ttgacggcgt tgggaatggc ggtctgctcg cccctgaggc ccctctcgac    2040
ttcggcaatg cggcgacggg ctgcaggctc actatgggac tggtcggggt gtacgacttc    2100
gatagcacgt tcatcggaga cgcctcgctc acaaagcgcc caatgggccg cgttctgaac    2160
ccgttgcgcg agatgggcgt acaggtcaaa tccgaggatg gtgaccgttt gcccgttacg    2220
ctgcgcgggc cgaagacgcc taccccgatt acctaccgcg tgccaatggc atccgcccag    2280
gtcaagtcag ccgtgctcct cgccggactg aacactccgg gcatcaccac ggtgatcgag    2340
cccatcatga ccagggatca taccgaaaag atgcttcagg ggtttggcgc caacctgacg    2400
gtcgagacgg acgctgacgg cgtcaggacc atccgccttg agggcagggg taaactgact    2460
ggccaagtca tcgatgttcc gggagacccg tcgtccacgg ccttcccgtt ggttgcggcg    2520
ctgctcgtgc cggggagtga cgtgaccatc ctgaacgtcc tcatgaaccc gaccaggacc    2580
ggcctgatcc tcacgcttca ggagatggga gccgacatcg aggtgatcaa cccgcgcctg    2640
gcaggcggtg aagacgttgc ggatctgcgc gtgcgctcct ctaccctgaa gggcgtgacg    2700
gtcccggaag atcgcgcgcc gtccatgata gacgagtatc ctattctggc cgtcgccgct    2760
gcgttcgccg aaggggccac ggtcatgaac ggtcttgagg aactccgcgt gaaggaatcg    2820
gatcgcctgt cggcggtggc caatggcctg aagctcaacg tgttgactg cgacgagggt    2880 gagacctcac tcgtggtccg tggccggcct gatggcaagg gcctcggcaa cgccagtgga    2940
gcggccgtcg ccacgcacct cgatcatcgc atcgcgatgt ccttcttggt gatgggtctc    3000
gtctcagaga acccggtgac cgtcgatgac gccacgatga tagcgacgag cttcccagag    3060
ttcatggatc tgatggcggg cctcgggggcc aagatcgaac tgtctgacac gaaggccgct    3120
tgaattcccg atcgttcaaa catttggcaa taaagtttct taagattgaa tcctgttgcc    3180
ggtcttgcga tgattatcat ataatttctg ttgaattacg ttaagcatgt aataattaac    3240
atgtaatgca tgacgttatt tatgagatgg gtttttatga ttagagtccc gcaattatac    3300
atttaatacg cgatagaaaa caaaatatag cgcgcaaact aggataaatt atcgcgcgcg    3360
gtgtcatcta tgttactaga tcggggatgg ggaattcggt accaaggacg cctacgaaaa    3420
ggttgtttgg gtttgcgaaa aggttgtttg aatttacgaa aagtttgctt ggatttacga    3480
aaagtttgct tggatttatg aaaagtttgt ttggatttat gaaagggttg tttagatgta    3540
tacatgattt attccttatt ttaaaattga aaaaaattga tttgtttatt ttattaattt    3600
tggatccaga aaaaatagtc tctctttggt ccatatatta gatgaatacc ctcgatacat    3660
atgaaataat atctaatgga aatcagacaa gttgatttgt attttgtatt ctatctatgc    3720
tctatatatt aaataggaag ttcttattct ttttgatctt tggaaagatc gaacacaaga    3780
tgctcctcat atctacagct gtgttaatgg gggcgtggtt tggtaatacg ccaatttggc    3840
cactattagt agataaaatg atttctttca cttcacaatc ccaaataatt cgcttaggag    3900
tcagtacata aagatttaat ttcatttcaa atgcgccaaa gccaaagcaa gccaccccctg    3960
```

-continued

```
caagaaataa atgaattcca aagatcttgg gcaaatccaa agaaggtttt cccgtccgct    4020
cgacctgtga agacctcct tgttgaaat gttcccaaaa ttcctaaaat aaaggaaaa      4080 a                                                                   4081
```

```
<210> SEQ ID NO 7
<211> LENGTH: 21
<212> TYPE: DNA
<213> ORGANISM: Artificial sequence
<220> FEATURE:
<221> NAME/KEY: misc_feature
<222> LOCATION: (1)..(21)
<223> OTHER INFORMATION: 5 prime insert primer sequence

<400> SEQUENCE: 7
gcggaaacgt ctccagtatt g                                             21

<210> SEQ ID NO 8
<211> LENGTH: 22
<212> TYPE: DNA
<213> ORGANISM: Artificial sequence
<220> FEATURE:
<221> NAME/KEY: misc_feature
<222> LOCATION: (1)..(22)
<223> OTHER INFORMATION: 5 prime flanking sequence primer

<400> SEQUENCE: 8
cgttaacaag cttctgcagg tc                                            22

<210> SEQ ID NO 9
<211> LENGTH: 19
<212> TYPE: DNA
<213> ORGANISM: Artificial sequence
<220> FEATURE:
<221> NAME/KEY: misc_feature
<222> LOCATION: (1)..(19)
<223> OTHER INFORMATION: 6FAM 5 prime region primer

<400> SEQUENCE: 9
ctcaactatt ggtaaagcc                                                19

<210> SEQ ID NO 10
<211> LENGTH: 25
<212> TYPE: DNA
<213> ORGANISM: Artificial sequence
<220> FEATURE:
<221> NAME/KEY: misc_feature
<222> LOCATION: (1)..(25)
<223> OTHER INFORMATION: 3 prime transgene insert primer

<400> SEQUENCE: 10
cgcttgaatt cccgatcgtt caaac                                         25

<210> SEQ ID NO 11
<211> LENGTH: 26
<212> TYPE: DNA
<213> ORGANISM: Artificial sequence
<220> FEATURE:
<221> NAME/KEY: misc_feature
<222> LOCATION: (1)..(26)
<223> OTHER INFORMATION: 3 prime flanking sequence primer

<400> SEQUENCE: 11
cccattaaca cagctgtaga tatgag                                        26

<210> SEQ ID NO 12
<211> LENGTH: 24
```

```
<212> TYPE: DNA
<213> ORGANISM: Artificial Sequence
<220> FEATURE:
<223> OTHER INFORMATION: Chemically synthesized Oligonucleotides

<400> SEQUENCE: 12
gaagacgtgg ttggaacgtc ttct                                        24

<210> SEQ ID NO 13
<211> LENGTH: 24
<212> TYPE: DNA
<213> ORGANISM: Artificial Sequence
<220> FEATURE:
<223> OTHER INFORMATION: Chemically synthesized Oligonucleotides

<400> SEQUENCE: 13
cggaccatca catcaatcca cttg                                        24

<210> SEQ ID NO 14
<211> LENGTH: 24
<212> TYPE: DNA
<213> ORGANISM: Artificial Sequence
<220> FEATURE:
<223> OTHER INFORMATION: Chemically synthesized Oligonucleotides

<400> SEQUENCE: 14
gattgaatcc tgttgccggt cttg                                        24

<210> SEQ ID NO 15
<211> LENGTH: 26
<212> TYPE: DNA
<213> ORGANISM: Artificial Sequence
<220> FEATURE:
<223> OTHER INFORMATION: Chemically synthesized Oligonucleotides

<400> SEQUENCE: 15
ggcaattgca gatgatagct caattc                                      26

<210> SEQ ID NO 16
<211> LENGTH: 25
<212> TYPE: DNA
<213> ORGANISM: Artificial Sequence
<220> FEATURE:
<223> OTHER INFORMATION: Chemically synthesized Oligonucleotides

<400> SEQUENCE: 16
ccttctttgg atttgcccaa gatct                                       25
```